US012690532B2

(12) United States Patent     (10) Patent No.:   US 12,690,532 B2

Messmer     (45) Date of Patent:    Jul. 28, 2026

(54) PENNYCRESS VARIETY B3

(71) Applicant: COVERCRESS INC., St. Louis, MO (US)

(72) Inventor: Mark Messmer, St. Louis, MO (US)

(73) Assignee: COVERCRESS INC., St. Louis, MO (US)

( * ) Notice: Subject to any disclaimer, the term of this patent is extended or adjusted under 35 U.S.C. 154(b) by 165 days.

(21) Appl. No.: 18/507,719

(22) Filed: Nov. 13, 2023

(65) Prior Publication Data

US 2024/0172620 A1     May 30, 2024

Related U.S. Application Data

(60) Provisional application No. 63/385,486, filed on Nov. 30, 2022.

(51) Int. Cl.
| | |
|---|---|
| *A01H 6/20* | (2018.01) |
| *A01H 5/10* | (2018.01) |
| *A01H 5/12* | (2018.01) |

(52) U.S. Cl.
CPC ................ *A01H 6/20* (2018.05); *A01H 5/10* (2013.01); *A01H 5/12* (2013.01)

(58) Field of Classification Search
None
See application file for complete search history.

(56) References Cited

U.S. PATENT DOCUMENTS

| | | | | |
|---|---|---|---|---|
| 10,709,151 | B2 * | 7/2020 | Ulmasov et al. ...... | A23K 10/30 |
| 10,988,772 | B2 | 4/2021 | Ulmasov et al. | |
| 11,408,008 | B2 | 8/2022 | Marks et al. | |
| 2018/0148735 | A1 | 5/2018 | Begemann et al. | |
| 2019/0053458 | A1 | 2/2019 | Marks et al. | |
| 2019/0225977 | A1 | 7/2019 | Ulmasov et al. | |
| 2020/0131523 | A1 | 4/2020 | Marks et al. | |
| 2022/0298519 | A1 | 9/2022 | Atwood et al. | |
| 2023/0263190 | A1 | 8/2023 | Ulmasov et al. | |
| 2023/0265450 | A1 | 8/2023 | Ulmasov et al. | |

OTHER PUBLICATIONS

Frels et al. (2019) Agronomy 9:302.*
Sedbrook et al. (2014) Plant Sci 227:122-32.*
Cubins et al. (2019) Agron. Sustain. Dev. 39:46.*

USDA (2023) Applying for a Plant Variety Certificate of Protection https://www.ams.usda.gov/services/pvpo/application-help/apply, accessed May 1, 2023).*
UPOV (2017) Explanatory Notes on Essentially Derived Varieties Under the 1991 Act of the UPOV Convention, n 14 & n. 30.*
Haun et al. (2011) Plant Physiol. 155:645-55.*
Großkinsky et al. (2015) J. Exp. Bot. 66:5429-40.*
Bairu et al. (2011) Plant Growth Regul 63:147-73.*
Chopra et al. (2020) Nature Food 1:84-91.*
Dorn et al. (2015) DNA Res 22(2):121-31.*
Fehr (1987) ("Backcross Method" in Principles of Cultivar Development (Macmillan Pub. Co. (New York)) pp. 360-376).*
Chopra et al., "Identification and stacking of crucial traits required for the domestication of pennycress," Nature Food, Jan. 2020, vol. 1, pp. 84-91.
Chopra et al., "Translational genomics using Arabidopsis as a model enables the characterization of pennycress genes through forward and reverse genetics," The Plant Journal, Dec. 2018, vol. 96, pp. 1093-1105.
Dorn et al., "A draft genome of field pennycress (*Thlaspi arvense*) provides tools for the domestication of a new winter biofuel crop," DNA Research, Apr. 2015, vol. 22, No. 2, pp. 121-131.
Garcia Navarrete et al., "Natural variation and improved genome annotation of the emerging biofuel crop field pennycress (*Thlaspi arvense*)," G3, Jun. 2022 , vol. 12, No. 6, 11 pages.
Marks, M., "Advancing Field Pennycress as a New Oilseed Biodiesel Feedstock that does not Require New Land Commitments," National Institute of Food and Agriculture, 2014 [retrieved on Apr. 23, 2024]. Retrieved from the Internet: <URL: https://portal.nifa.usda.gov/web/crisprojectpages/1004021-advancing-field-pennycress-as-a-new-oilseed-biodiesel-feedstock-that-does-not-require-new-land-commitments.html>, 13 pages.
Nunn et al., "Chromosome-level *Thlaspi arvense* genome provides new tools for translational research and for a newly domesticated cash cover crop of the cooler climates," Plant Biotechnology Journal, May 2022, vol. 20, pp. 944-963.
Sedbrook et al., "New approaches to facilitate rapid domestication of a wild plant to an oilseed crop: Example pennycress (*Thlaspi arvense* L.)," Plant Science, Oct. 2014, vol. 227, pp. 122-132.
U.S. Appl. No. 18/507,866, filed Nov. 13, 2023, 69 pages.

* cited by examiner

*Primary Examiner* — Russell T Boggs
(74) *Attorney, Agent, or Firm* — McKee, Voorhees & Sease, PLC

(57) ABSTRACT

A novel pennycress variety designated B3 is provided. This disclosure thus relates to the seeds of pennycress variety B3, to the plants of pennycress variety B3, to plant parts of pennycress variety B3, to methods for producing a pennycress plant by crossing a plant of pennycress variety B3 with a plant of another pennycress variety, and to methods for producing a plant of pennycress variety B3 containing in its genetic material one or more gene edits, backcross conversion traits, or transgenes and to the pennycress plants and plant parts produced by those methods.

28 Claims, No Drawings

PENNYCRESS VARIETY B3

CROSS-REFERENCE TO RELATED APPLICATION

This application claims priority under 35 U.S.C. § 119 to Provisional Application U.S. Ser. No. 63/385,486, filed on Nov. 30, 2022, which is herein incorporated by reference in its entirety including without limitation, the specification, claims, and abstract, as well as any figures, tables, or examples thereof.

TECHNICAL FIELD

The present disclosure relates to the field of plant breeding. In particular, this disclosure relates to a new pennycress variety designated B3.

BACKGROUND

Field Pennycress *Thlaspi arvense* L. (common names: fanweed, stinkweed, field pennycress), hereafter referred to as Pennycress or pennycress, is a novel winter oilseed and covercrop that provides a source of low carbon liquid biofuel feedstock and also helps to protect soil from erosion, prevent the loss of farm-field nitrogen into water systems, and retain nutrients and residues to improve soil productivity. While it is well established that cover crops provide agronomic and ecological benefits to agriculture and environment, only 5% of farmers today are using them. One reason is economics—it requires on average ~$30-40/acre to grow a cover crop on the land that is otherwise idle between two seasons of cash crops such as corn and soy. Farmers do not realize sufficient short-term incentives to invest in the long-term benefits to their soils. Recently, it has been recognized that pennycress could be used as a novel cover crop, because in addition to providing cover crop benefits, it is an oilseed with its oil being useful as a biofuel. Extensive testing indicates that it can be inter-seeded over standing corn or soybeans in early fall just prior to summer crop harvest, seeded from a combine during summer crop harvest, or seeded from a tillage implement immediately following summer crop harvest. The resulting crop is harvested in spring prior to soybean or corn planting (in appropriate climates). As such, its growth and development requires minimal incremental inputs (e.g., no/minimum tillage, low nitrogen, no insecticides or herbicides). Pennycress also does not directly compete with food crops when grown during the winter season for energy production, and the recovered oil and meal can provide an additional source of income for farmers.

Pennycress is a winter annual belonging to the Brassicaceae (mustard) family. It is related to cultivated crops, rapeseed and canola, which are also members of the Brassicaceae family. Pennycress seeds are smaller than canola, but they are also high in oil content. They typically contain 30-34% oil, which is over 50 percent higher than the level found in soybean, and the oil has a very low saturated fat content (~4%). Pennycress represents a clear opportunity for sustainable optimization of agricultural systems. For example, in the US Midwest, ~35M acres that remain idle could be planted with pennycress after a summer crop is harvested and before the next year's crop is planted in the spring. Pennycress can serve as an important winter cover crop working within the no/low-till corn and soybean rotation to guard against soil erosion and improve overall field soil nitrogen and pest management, providing a living cover throughout the winter and spring seasons.

There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals. The goal is to combine in a single variety or hybrid an improved combination of desirable traits from the parental germplasm.

SUMMARY

There is provided a novel pennycress variety designated B3. This disclosure thus relates to the seeds of pennycress variety B3, to the plants of pennycress variety B3, to plant parts of pennycress variety B3, to methods for producing seed of a pennycress variety produced by crossing the pennycress variety B3 with itself or with another pennycress variety, and to methods for producing a pennycress variety containing in its genetic material one or more directly gene edited or backcross conversion traits or transgenes and to the directly gene edited and backcross conversion pennycress plants and plant parts produced by those methods. This disclosure further relates to hybrid pennycress seeds and plants produced by crossing pennycress variety B3 with another pennycress variety. This disclosure also relates to pennycress varieties and plant parts derived from pennycress variety B3, to methods for producing other pennycress varieties derived from pennycress variety B3 and to the pennycress varieties and their parts derived using those methods.

The disclosure also provides a plant or a progeny having all of the physiological and morphological characteristics of pennycress variety B3, when grown under the same environmental conditions. In another embodiment, the plant or progeny has all or all but one, two, or three of the physiological and morphological characteristics of pennycress variety B3 when grown under the same environmental conditions and e.g., evaluated at significance levels of 1%, 5%, or 10% significance (which can be expressed as a p-value) for quantitative characteristics. In another embodiment, the plant or progeny has all or all but one, two, or three of the physiological and morphological characteristics as listed in Table 1 of pennycress variety B3 when measured under the same environmental conditions and e.g., evaluated at significance levels of 1%, 5%, or 10% significance (which can also be expressed as a p value) for quantitative characteristics.

In another embodiment, the present disclosure provides regenerable cells for use in tissue culture of pennycress variety B3. In certain embodiments, the tissue culture may be capable of regenerating plants having essentially all of the physiological and morphological characteristics of the foregoing pennycress plant, and of regenerating plants having substantially the same genotype as the foregoing pennycress plant. Still further, the present disclosure provides pennycress plants regenerated from the tissue cultures disclosed herein.

The disclosure also provides methods of multiplication or propagation of pennycress plants of the disclosure, which can be accomplished using any method known in the art, for example, via vegetative propagation and/or seed. Still further, as another embodiment, the disclosure provides a method of vegetatively propagating a plant of pennycress variety B3. In a non-limiting example, the method comprises: (a) collecting a plant part capable of being propagated from a plant of pennycress variety B3; (b) producing at least a first rooted plant from the plant part. The disclosure also encompasses the plantlets and plants produced by these methods.

This disclosure further relates to the $F_1$ hybrid pennycress plants and plant parts grown from the hybrid seed produced by crossing pennycress variety B3 to a second pennycress plant. Still further included in the disclosure are the seeds of an $F_1$ hybrid plant produced with the pennycress variety B3 as one parent, the second generation ($F_2$) hybrid pennycress plant grown from the seed of the $F_1$ hybrid plant, and the seeds of the $F_2$ hybrid plant. Thus, any such methods using the pennycress variety B3 are part of this disclosure: selfing, backcrosses, hybrid production, crosses to populations, and the like. All plants produced using pennycress variety B3 as at least one parent are within the scope of this disclosure. Advantageously, the pennycress variety could be used in crosses with other, different, pennycress plants to produce first generation ($F_1$) pennycress hybrid seeds and plants with superior characteristics. Newly developed $F_1$ hybrids can be reproduced via asexual reproduction.

This disclosure also relates to pennycress plants or varieties and plant parts derived from pennycress variety B3. Still yet another embodiment of the disclosure is a method of producing a pennycress plant derived from the pennycress variety B3, the method comprising the steps of: (a) preparing a progeny plant derived from pennycress variety B3 by crossing a plant of the pennycress variety B3 with a second pennycress plant; and (b) crossing the progeny plant with itself or a second plant to produce a seed of a progeny plant of a subsequent generation which is derived from a plant of the pennycress variety B3. In further embodiments of the disclosure, the method may additionally comprise: (c) growing a progeny plant of a subsequent generation from the seed of a progeny plant of a subsequent generation and crossing the progeny plant of a subsequent generation with itself or a second plant; and repeating the steps for an additional 2-10 generations to produce a pennycress plant derived from the pennycress variety B3. The plant derived from pennycress variety B3 may be an inbred line, and the aforementioned repeated crossing steps may be defined as comprising sufficient inbreeding to produce the inbred line. In the method, it may be desirable to select particular plants resulting from step (c) for continued crossing according to steps (b) and (c). By selecting plants having one or more desirable traits, a plant derived from pennycress variety B3 is obtained which possesses some of the desirable traits of the line as well as potentially other selected traits. Also provided by the disclosure is a plant produced by this and the other methods of the disclosure.

In another embodiment, the method of producing a pennycress plant derived from the pennycress variety B3 further comprises: (a) crossing the pennycress variety B3-derived pennycress plant with itself or another pennycress plant to yield additional pennycress variety B3-derived progeny pennycress seed; (b) growing the progeny pennycress seed of step (a) under plant growth conditions to yield additional pennycress variety B3-derived pennycress plants; and (c) repeating the crossing and growing steps of (a) and (b) to generate further pennycress variety B3-derived pennycress plants. In specific embodiments, steps (a) and (b) may be repeated at least 1, 2, 3, 4, or 5 or more times as desired. The disclosure still further provides a pennycress plant produced by this and the foregoing methods.

Another embodiment of the disclosure is a pennycress plant of variety B3 further comprising a mutation of an endogenous gene. In certain embodiments, the pennycress plant is defined as comprising the mutation of the endogenous gene and otherwise capable of expressing all of the morphological and physiological characteristics of the pennycress variety B3. In another embodiment, the pennycress plant has all of the physiological and morphological characteristics listed in Table 2 when measured under the same environmental conditions and e.g., evaluated at significance levels of 1%, 5%, or 10% significance (which can also be expressed as a p value) for quantitative characteristics. In particular embodiments, the mutation of the endogenous gene is a loss-of-function mutation. The mutation of the endogenous gene may confer a desired trait upon the plant, including herbicide resistance, insect or pest resistance, resistance to bacterial, fungal, or viral disease, reduced seed fiber content, earlier maturity, modified seed color, increased or modified seed protein composition, increased or modified seed oil content or fatty acid composition, reduced seed glucosinolate content, or shatter resistance. In certain embodiments, the desired trait comprises reduced seed fiber content, modified seed color, increased or modified seed protein composition, and increased or modified seed oil content or fatty acid composition.

The disclosure also provides a method of producing a modified pennycress plant, wherein the method comprises mutating an endogenous gene in a pennycress plant or plant part of pennycress variety B3, and wherein the mutated plant otherwise retains all of the physiological and morphological characteristics of pennycress variety B3 and contains a desired trait. In certain embodiments, the endogenous gene is mutated by targeted gene editing (e.g., a CRISPR/Cas system). In other embodiments, the endogenous gene is mutated through subjecting seed or plant parts of pennycress variety B3 or progeny of pennycress variety B3 to DNA mutagenesis agents such as Ethyl Methanesulfonate (EMS), UV radiation, X-ray radiation, transposable elements, or other forms of creating discrete changes in the DNA structure. Also provided by the disclosure is a plant produced by this and the other methods of the disclosure.

The disclosure also relates to methods for producing a pennycress plant containing in its genetic material one or more transgenes and to the transgenic pennycress plants produced by those methods.

The disclosure further relates to methods for genetically modifying a pennycress plant of the pennycress variety B3 and to the modified pennycress plants produced by those methods. The genetic modification methods may include, but are not limited to mutation, genome editing, RNA interference, gene silencing, backcross conversion, genetic transformation, single and multiple gene conversion, and/or direct gene transfer. The disclosure further relates to a genetically modified pennycress plant produced by the above methods, wherein the genetically modified pennycress plant comprises the genetic modification and otherwise comprises all of the physiological and morphological characteristics of pennycress variety B3.

Another embodiment of the disclosure is a pennycress plant further comprising a single locus conversion and otherwise capable of expressing all of the morphological and physiological characteristics of the pennycress variety B3. In particular embodiments, the single locus conversion may comprise a transgenic gene which has been introduced by genetic transformation into the pennycress variety B3 or a progenitor thereof. A transgenic or non-transgenic single locus conversion can also be introduced by backcrossing, as is well known in the art. In still other embodiments of the disclosure, the single locus conversion may comprise a dominant or recessive allele. The locus conversion may confer potentially any trait upon the single locus converted plant, including herbicide resistance, insect or pest resistance, resistance to bacterial, fungal, or viral disease, reduced seed fiber content, earlier maturity, modified seed color, increased or modified seed protein composition, increased or modified seed oil content or fatty acid composition, reduced seed glucosinolate content, and shatter resistance. The trait may be, for example, conferred by a naturally occurring gene introduced into the genome of the variety by backcrossing, a natural or induced mutation, or a transgene introduced through genetic transformation techniques into the plant or a progenitor of any previous generation thereof. When introduced through transformation, a genetic locus may comprise one or more transgenes integrated at a single chromosomal location.

In still yet another embodiment, the genetic complement of the pennycress variety B3 is provided. The phrase "genetic complement" is used to refer to the aggregate of nucleotide sequences, the expression of which sequences defines the phenotype of, in the present case, a pennycress plant, or a cell or tissue of that plant. A genetic complement thus represents the genetic makeup of a cell, tissue or plant, and a hybrid genetic complement represents the genetic makeup of a hybrid cell, tissue or plant. The disclosure thus provides pennycress plant cells that have a genetic complement in accordance with the pennycress plant cells disclosed herein, and plants, seeds and plants containing such cells. Plant genetic complements may be assessed by genetic marker profiles, and by the expression of phenotypic traits that are characteristic of the expression of the genetic complement, e.g., isozyme typing profiles.

In still yet another embodiment, the disclosure provides a method of determining the genotype of a plant of pennycress variety B3 comprising detecting in the genome of the plant at least a first polymorphism. The method may, in certain embodiments, comprise detecting a plurality of polymorphisms in the genome of the plant. The method may further comprise storing the results of the step of detecting the plurality of polymorphisms on a computer readable medium. The disclosure further provides a computer readable medium produced by such a method.

The disclosure further provides methods for developing a pennycress variety in a pennycress plant breeding program using plant breeding techniques including but not limited to recurrent selection, backcrossing, pedigree breeding, genetic marker enhanced selection, gene editing, and transformation. Pennycress seeds, plants, and parts thereof, produced by such breeding methods are also part of the disclosure.

DETAILED DESCRIPTION

So that the present disclosure may be more readily understood, certain terms are first defined. Unless defined otherwise, all technical and scientific terms used herein have the same meaning as commonly understood by one of ordinary skill in the art to which embodiments of the disclosure pertain. Many methods and materials similar, modified, or equivalent to those described herein can be used in the practice of the embodiments of the present disclosure without undue experimentation, the preferred materials and methods are described herein. In describing and claiming the embodiments of the present disclosure, the following terminology will be used in accordance with the definitions set out below.

It is to be understood that all terminology used herein is for the purpose of describing particular embodiments only and is not intended to be limiting in any manner or scope. For example, as used in this specification and the appended claims, the singular forms "a," "an" and "the" can include plural referents unless the content clearly indicates otherwise. Similarly, the word "or" is intended to include "and" unless the context clearly indicate otherwise. The word "or" means any one member of a particular list and also includes any combination of members of that list. Further, all units, prefixes, and symbols may be denoted in its SI accepted form.

An "allele" is any of one or more alternative forms of a genetic sequence. In a diploid cell or organism, the two alleles of a given genetic sequence occupy corresponding loci on a pair of homologous chromosomes.

The term "backcrossing" refers to a process in which a breeder crosses progeny to one of the parents one or more times, for example, a first-generation hybrid $F_1$ with one of the parental genotype of the $F_1$ hybrid.

A "cell" as used herein includes a plant cell, whether isolated, in tissue culture or incorporated in a plant or plant part. The cell can be a cell, such as a somatic cell, of the variety having the same set of chromosomes as the cells of the deposited seed, or, if the cell contains a locus conversion or transgene, otherwise having the same or essentially the same set of chromosomes as the cells of the deposited seed.

A "commodity plant product" refers to any composition or product that is comprised of material derived from a plant, seed, plant cell, or plant part of the present disclosure. Commodity plant products may be sold to consumers and can be viable or nonviable. Nonviable commodity products include but are not limited to nonviable seeds and grains; processed seeds, seed parts, and plant parts; dehydrated plant tissue, frozen plant tissue, and processed plant tissue; seeds and plant parts processed for animal feed for terrestrial and/or aquatic animal consumption, oil, meal, flour, fiber, crushed of whole grain, and any other food for human or animal consumption; biomasses and fuel products; and raw material in industry.

As used herein, "genome editing" or "gene editing" refers to a type of genetic engineering in which DNA is inserted, replaced, modified, or removed from a genome using artificially engineered nucleases. Examples include but are not limited to use of zinc finger nucleases (ZFNs), TAL effector nucleases (TALENs), meganucleases, CRISPR/Cas9, and other CRISPR related technologies.

A "locus conversion" (also called a "trait conversion" or "gene conversion") refers to a plant or plants within a variety or line that have been modified in a manner that retains the overall genetics and phenotypes of the variety and further comprises one or more loci with a specific desired trait, such as but not limited to insect or pest control, disease control or herbicide tolerance. Examples of single locus conversions include mutant genes, transgenes and native traits finely mapped to a single locus. One or more locus conversion traits may be introduced into a single variety.

As used herein, the term "plant" includes plant cells, plant protoplasts, plant tissue, plant cells of tissue culture from which pennycress plants can be regenerated, plant calli, plant clumps, and plant cells that are intact in plants, or parts of plants such as pollen, flowers, seeds, leaves, stems, and the like.

As used herein, "plant part" includes any part of a plant, such as a plant organ, a plant cell, a plant protoplast, a plant cell tissue culture or a tissue culture from which a whole plant can be regenerated, a plant cell that is intact in a plant, a clone, a micropropagation, plant callus, a plant cell clump, a plant transplant, a vegetative propagation, a pod, a part of a pod, a leaf, a part of a leaf, pollen, an ovule, an embryo, a petiole, a shoot or a part thereof, a stem or a part thereof, a root or a part thereof, a root tip, a cutting, a seed, a part of a seed, a hypocotyl, a cotyledon, a scion, a graft, a stock, a rootstock, pericarp, a pistil, an anther, or a flower. Seed can be mature or immature. Pollen or ovules may be viable or non-viable. Also, any developmental stage is included, such as seedlings, cuttings prior or after rooting, mature plants or leaves.

As used herein, the term "progeny" refers to any plant resulting from a vegetative or sexual reproduction from one or more parent plants or descendants thereof. For instance, a progeny plant may be obtained by cloning or selfing of a parent plant or by crossing two parent plants and include selfings as well as the F1 or F2 or subsequent generations. An F1 is a first-generation progeny produced from parents at least one of which is used for the first time as donor of a trait, while offspring of second generation (F2) or subsequent generations (F3, F4, etc.) are specimens produced from selfings of F1's F2's etc. An F1 may thus be (and usually is) a hybrid resulting from a cross between two true breeding parents (true-breeding is homozygous for a trait), while an F2 may be (and usually is) a progeny resulting from self-pollination of said F1 hybrids.

A "single locus converted" plant refers to plants which are developed by a plant breeding technique called backcrossing or via genetic engineering (e.g., gene editing or insertion of an exogenous gene through transformation) wherein essentially all of the morphological and physiological characteristics of a variety are recovered in addition to the desired trait or characteristics conferred by the single locus transferred into the variety via the backcrossing technique or via genetic engineering. A single locus may comprise one gene, or in the case of transgenic plants, one or more transgenes integrated into the host genome at a single site (locus).

A "transgene" refers to a nucleic acid of interest that can be introduced into the genome of a plant by genetic engineering techniques (e.g., transformation).

Pennycress Variety B3

Pennycress variety B3 originated in year 2015 from a manmade cross made in Mexico, Missouri between two proprietary, not commercially available, wild-collected parents designated 1228 and 1036 selected for their high yield characteristics, followed by at least five generations of modified bulk breeding and selection. Pennycress variety B3 is genetically stable and uniform.

A description of pennycress variety B3 is provided in Table 1.

TABLE 1

| PLANT | |
|---|---|
| Plant Height (cm) | 74.20 |
| STEM | |
| Stem Diameter (mm) | 6.02 |
| Stem Anthocyanin | Weak (2.0) |
| LEAVES | |
| Leaf Color | Medium Green (2.2) |
| Leaf Margin Serration | Medium (2.0) |
| FLOWERS | |
| Flower Maturity Class | Medium (3.40) |

TABLE 1-continued

| PODS | |
|---|---|
| Seeds Per Pod | 11.46 |
| Pedicel Length (mm) | 10.63 |
| Pod Ripening Class | Medium |
| SEED | |
| Seed Color | Black |
| 1000 Seed Weight (g) | 1.11 |
| GRAIN QUALITY | |
| Oil % | 32.55 |
| Erucic acid % of total oil | 43.74 |
| Acid Detergent Fiber | 22.04 |
| Acid Neutral Detergent Fiber | 29.87 |
| Protein % | 21.13 |
| Sinigrin Content (μmol per g) | 97.18 |

Table 2 provides a description of pennycress B3:WG:B28312C:EDIT, a gene edited plant of pennycress variety B3 having reduced seed fiber content as well as modified seed color, increased seed protein content, reduced erucic acid content, and increased seed oil content. Use of gene editing to achieve loss-of-function mutations in endogenous pennycress genes to confer plants with reduced seed coat fiber, lighter-colored seed coat due to reduced proanthocyanidins content, increased protein content, and/or higher seed oil and reduced erucic acid content are disclosed in U.S. Pat. Nos. 10,709,151 and 11,396,657, which are hereby incorporated by reference.

TABLE 2

| PLANT | |
|---|---|
| Plant Height (cm) | 75.20 |
| STEM | |
| Stem Diameter (mm) | 5.27 |
| Stem Anthocyanin | Weak (2.4) |
| LEAVES | |
| Leaf Color | Medium dark green (2.7) |
| Leaf Margin Serration | Strong (2.7) |
| FLOWERS | |
| Flower Maturity Class | Medium (2.9) |
| PODS | |
| Seeds Per Pod | 9.90 |
| Pedicel Length (mm) | 9.93 |
| Pod Ripening Class | Medium-Late |
| SEED | |
| Seed Color | Yellow |
| 1000 Seed Weight (g) | 1.22 |
| GRAIN QUALITY | |
| Oil % | 40.18 |
| Erucic acid % of total oil | 5.91 |
| Acid Detergent Fiber | 18.22 |
| Acid Neutral Detergent Fiber | 17.08 |
| Protein % | 28.43 |
| Sinigrin Content (μmol per g) | 102.15 |

Table 3 shows results from a spring 2022 data collection. The results provide a comparison of pennycress variety B3, B3:WG:B28312C:EDIT, wild parents, and public wild type checks Elizabeth and Beecher. Pennycress varieties B28 and B73 are also shown. Table 4 provides a description of the traits listed.

TABLE 3

|  | SEEDCOLOR | OILNIRARV | OILERUCIC | SINIGRIN | FIBERADF |
|---|---|---|---|---|---|
| Elizabeth | Black | 34.47 | 43.38 | 89.65 | 22.32 |
| Beecher | Black | 32.76 | 44.59 | 96.33 | 20.80 |
| B3 Wild Type Parent A | Black | 30.44 | 44.29 | 111.60 | 22.61 |
| B3 | Black | 32.55 | 43.74 | 97.18 | 22.04 |
| B3:WG:B28312C:EDIT | Yellow | 40.18 | 5.91 | 102.15 | 18.22 |
| B3 Wild Type Parent B | Black | 32.80 | 43.05 | 91.04 | 20.24 |
| B28 Wild Type Parent A | Black | 32.80 | 43.05 | 91.04 | 20.24 |
| B28 | Black | 32.69 | 42.37 | 97.66 | 22.19 |
| B28: WG:B29336A:EDIT | Yellow | 37.84 | 3.65 | 109.86 | 19.13 |
| B28 Wild Type Parent B | Black | 34.19 | 38.53 | 89.92 | 20.26 |
| B73 Wild Type Parent A | Black | 33.88 | 46.46 | 102.20 | 16.97 |
| B73 | Black | 33.67 | 45.09 | 102.50 | 18.30 |
| B73:WG:B28837A:EDIT | Yellow | 38.49 | 8.85 | 107.03 | 18.21 |
| B73 Wild Type Parent B | Black | 34.46 | 42.78 | 92.00 | 22.70 |
| No. of Reps |  | 10 | 10 | 10 | 10 |
| Grand Mean |  | 34.49 | 34.82 | 99.16 | 20.31 |
| Error d.f. |  | 106.00 | 106.00 | 106.00 | 106.00 |
| R-Square |  | 0.92 | 0.99 | 0.80 | 0.70 |
| 2 * Error |  | 0.76 | 1.45 | 3.60 | 1.43 |
| Alpha level |  | 0.05 | 0.05 | 0.05 | 0.05 |
| LSD |  | 0.63 | 1.21 | 2.99 | 1.19 |
| SED |  | 0.38 | 0.73 | 1.80 | 0.72 |
| C.V. |  | 2.46 | 4.66 | 4.06 | 7.87 |
| Heritability |  | 0.91 | 0.99 | 0.77 | 0.59 |
| Min. Mean |  | 30.44 | 3.65 | 89.65 | 16.97 |
| Max. Mean |  | 40.18 | 46.46 | 111.60 | 22.70 |
| Min. Plot |  | 28.3 | 0.8 | 79.7 | 13.6 |
| Max. Plot |  | 42.3 | 48.3 | 115.9 | 26.0 |
| Range |  | 9.75 | 42.82 | 21.95 | 5.73 |
| Residual |  | 0.72 | 2.64 | 16.23 | 2.56 |
| Method |  | ACB | ACB | ACB | ACB |

|  | FIBERANDF | PROTEINPCT | Leaf color rating | Leaf Color | Leaf margin serration rating | Leaf margin serration |
|---|---|---|---|---|---|---|
| Elizabeth | 28.26 | 19.34 | 1.30 | Light Green | 1.40 | Weak |
| Beecher | 28.69 | 19.75 | 2.10 | Medium Green | 2.10 | Medium |
| B3 Wild Type Parent A | 31.57 | 20.11 | 1.90 | Medium Green | 2.30 | Medium |
| B3 | 29.87 | 21.13 | 2.20 | Medium Green | 2.00 | Medium |
| B3:WG:B28312C:EDIT | 17.08 | 28.43 | 2.70 | Medium dark green | 2.70 | Strong |
| B3 Wild Type Parent B | 28.50 | 19.92 | 1.20 | Light Green | 1.00 | Weak |
| B28 Wild Type Parent A | 28.50 | 19.92 | 1.20 | Light Green | 1.00 | Weak |
| B28 | 29.11 | 21.92 | 1.80 | Medium Green | 2.30 | Medium |
| B28:WG:B29336A:EDIT | 17.72 | 29.01 | 2.10 | Medium Green | 2.00 | Medium |
| B28 Wild Type Parent B | 27.26 | 21.37 | 1.60 | Medium Green | 2.10 | Medium |
| B73 Wild Type Parent A | 27.16 | 21.41 | 2.00 | Medium Green | 2.30 | Medium |
| B73 | 27.53 | 21.54 | 2.70 | Medium dark green | 2.90 | Strong |
| B73:WG:B28837A:EDIT | 18.37 | 27.12 | 2.90 | Medium dark green | 2.00 | Medium |
| B73 Wild Type Parent B | 28.27 | 19.61 | 1.80 | Medium Green | 2.00 | Medium |
| No. of Reps | 10 | 10 | 10 |  | 10 |  |
| Grand Mean | 26.11 | 22.36 | 2.02 |  | 2.08 |  |
| Error d.f. | 106.00 | 106.00 | 108.00 |  | 107.00 |  |
| R-Square | 0.99 | 0.97 | 0.62 |  | 0.66 |  |
| 2 * Error | 0.57 | 0.54 | 0.40 |  | 0.33 |  |
| Alpha level | 0.05 | 0.05 | 0.05 |  | 0.05 |  |
| LSD | 0.47 | 0.45 | 0.33 |  | 0.28 |  |
| SED | 0.28 | 0.27 | 0.20 |  | 0.17 |  |
| C.V. | 2.43 | 2.71 | 22.03 |  | 17.85 |  |
| Heritability | 0.98 | 0.97 | 0.56 |  | 0.62 |  |
| Min. Mean | 17.08 | 19.34 | 1.20 |  | 1.00 |  |
| Max. Mean | 31.57 | 29.01 | 2.90 |  | 2.90 |  |

TABLE 3-continued

| | | | | |
|---|---|---|---|---|
| Min. Plot | 16.5 | 18.0 | 1.0 | 1.0 |
| Max. Plot | 32.1 | 30.2 | 4.0 | 3.0 |
| Range | 14.49 | 9.68 | 1.70 | 1.90 |
| Residual | 0.40 | 0.37 | 0.20 | 0.14 |
| Method | ACB | ACB | ACB | ACB |

| | MSTNIRARV | Pedicel Length | PLANTHGTCM | SEED1000 | Seeds Per Pod |
|---|---|---|---|---|---|
| Elizabeth | 8.58 | 11.70 | 85.00 | 1.07 | 12.72 |
| Beecher | 8.93 | 10.47 | 70.20 | 1.11 | 11.70 |
| B3 Wild Type Parent A | 9.41 | 9.20 | 76.70 | 1.41 | 7.98 |
| B3 | 10.03 | 10.63 | 74.20 | 1.11 | 11.46 |
| B3:WG:B28312C:EDIT | 7.03 | 9.93 | 75.20 | 1.22 | 9.90 |
| B3 Wild Type Parent B | 9.04 | 11.53 | 79.75 | 1.15 | 11.02 |
| B28 Wild Type Parent A | 9.04 | 11.53 | 79.75 | 1.15 | 11.02 |
| B28 | 9.92 | 9.73 | 71.90 | 1.06 | 11.20 |
| B28:WG:B29336A:EDIT | 7.27 | 10.03 | 69.00 | 1.01 | 10.68 |
| B28 Wild Type Parent B | 9.58 | 11.43 | 87.70 | 1.15 | 11.30 |
| B73 Wild Type Parent A | 9.25 | 8.64 | 75.10 | 1.14 | 10.88 |
| B73 | 9.25 | 9.67 | 74.50 | 1.15 | 9.47 |
| B73:WG:B28837A:EDIT | 7.17 | 9.62 | 69.42 | 1.18 | 9.21 |
| B73 Wild Type Parent B | 8.73 | 11.64 | 83.90 | 1.08 | 12.74 |
| No. of Reps | 10 | 10 | 10 | 10 | 10 |
| Grand Mean | 8.78 | 10.33 | 76.35 | 1.14 | 10.79 |
| Error d.f. | 106.00 | 104.00 | 106.00 | 106.00 | 106.00 |
| R-Square | 0.94 | 0.74 | 0.59 | 0.72 | 0.63 |
| 2 * Error | 0.25 | 0.62 | 5.03 | 0.06 | 1.05 |
| Alpha level | 0.05 | 0.05 | 0.05 | 0.05 | 0.05 |
| LSD | 0.20 | 0.52 | 4.17 | 0.05 | 0.87 |
| SED | 0.12 | 0.31 | 2.51 | 0.03 | 0.52 |
| C.V. | 3.12 | 6.74 | 7.36 | 5.82 | 10.87 |
| Heritability | 0.93 | 0.66 | 0.52 | 0.67 | 0.55 |
| Min. Mean | 7.03 | 8.64 | 69.00 | 1.01 | 7.98 |
| Max. Mean | 10.03 | 11.70 | 87.70 | 1.41 | 12.74 |
| Min. Plot | 6.7 | 8.0 | 59.0 | 0.8 | 4.2 |
| Max. Plot | 10.7 | 13.7 | 100.0 | 1.6 | 14.6 |
| Range | 3.00 | 3.06 | 18.70 | 0.40 | 4.76 |
| Residual | 0.08 | 0.48 | 31.59 | 0.00 | 1.38 |
| Method | ACB | ACB | ACB | ACB | ACB |

| | Stem anthocyanin rating | Stem anthocyanin | Stem Diameter | Flower Mat Class Rating | Flower Mat Class Rating | Pod Ripening Class |
|---|---|---|---|---|---|---|
| Elizabeth | 3.50 | Strong | 5.77 | 3.80 | Medium-Late | Medium |
| Beecher | 2.40 | Weak | 5.63 | 3.30 | Medium | Medium |
| B3 Wild Type Parent A | 2.30 | Weak | 6.46 | 2.70 | Medium | Late |
| B3 | 2.00 | Weak | 6.02 | 3.40 | Medium | Medium |
| B3:WG:B28312C:EDIT | 2.40 | Weak | 5.27 | 2.90 | Medium | Medium-Late |
| B3 Wild Type Parent B | 2.10 | Weak | 5.94 | 2.70 | Medium | Medium |
| B28 Wild Type Parent A | 2.10 | Weak | 5.94 | 2.70 | Medium | |
| B28 | 2.10 | Weak | 4.89 | 4.00 | Medium-Late | Medium |
| B28:WG:B29336A:EDIT | 2.30 | Weak | 4.58 | 1.70 | Early | Medium Late |
| B28 Wild Type Parent B | 2.80 | Medium | 5.86 | 3.80 | Medium-Late | |
| B73 Wild Type Parent A | 3.00 | Medium | 5.35 | 4.30 | Medium-Late | |
| B73 | 2.70 | Medium | 4.64 | 3.30 | Medium-Late | Medium Early |
| B73:WG:B28837A:EDIT | 1.00 | Absent | 4.97 | 1.70 | Early | Medium |
| B73 Wild Type Parent B | 3.30 | Medium | 5.45 | 4.40 | Medium-Late | |
| No. of Reps | 10 | | 10 | 10 | | |
| Grand Mean | 2.45 | | 5.45 | 3.23 | | |
| Error d.f. | 107.00 | | 107.00 | 107.00 | | |
| R-Square | 0.67 | | 0.51 | 0.57 | | |
| 2 * Error | 0.44 | | 0.56 | 0.77 | | |
| Alpha level | 0.05 | | 0.05 | 0.05 | | |

TABLE 3-continued

| LSD | 0.37 | 0.46 | 0.64 |
|---|---|---|---|
| SED | 0.22 | 0.28 | 0.38 |
| C.V. | 20.13 | 11.44 | 26.57 |
| Heritability | 0.61 | 0.42 | 0.48 |
| Min. Mean | 1.00 | 4.58 | 1.70 |
| Max. Mean | 3.50 | 6.46 | 4.40 |
| Min. Plot | 1.0 | 3.0 | 1.0 |
| Max. Plot | 4.0 | 7.4 | 6.0 |
| Range | 2.50 | 1.88 | 2.70 |
| Residual | 0.24 | 0.39 | 0.74 |
| Method | ACB | ACB | ACB |

TABLE 4

| Trait | Description |
|---|---|
| FIBERADF | Acid Detergent Fiber via NIR. Approximately 1 gram of mature seed was placed in an individual clear glass vial for NIR analysis. |
| FIBERANDF | Acid Neutral Detergent Fiber via NIR. Approximately 1 gram of mature seed was placed in an individual clear glass vial for NIR analysis. |
| Flower Mat Class Rating | Maturity class: 1 = Very early, 2 = early, 3 = medium early, 4 = medium late, 5 = late, 6 = very late. Value corresponds to the first open flower observed (From May 9th to May 15th, 2022). |
| Flowering Maturity Class | Verbal rendition of Flower Maturity class rating. |
| Leaf color | Verbal rendition of leaf color at late rosette stage. Visual observation of the predominant leaf color from fully developed leaves at the rosette stage. |
| Leaf color rating | Number associated with leaf color. 1 = Light Green, 2 = medium green, 3 = medium dark green, 4 = dark green. |
| Leaf Margin Serration | Verbal rendition of depth of serrations on leaf margins in rosette stage. Visual observation of the predominant leaf margin serration from fully developed leaves at the rosette stage. |
| Leaf margin serration rating | Depth of serration of leaf margins in rosette stage: 1 = Weak, 2 = medium, 3 = strong. |
| MSTNIRARV | Moisture taken with NIR on dried samples. |
| OILERUCIC | Erucic acid percent of total oil. Approximately 1 gram of mature seed was placed in an individual clear glass vial for NIR analysis. |
| OILNIRARV | Oil % as measured NIR. Approximately 1 gram of mature seed was placed in an individual clear glass vial for NIR analysis. |
| Pedicel Length | Pedicel length midway on the main flower stem in mm. Length was measured with a digital caliper. The value reported corresponds to the average length of three pedicels measured from the center of the main stem. |
| PLANTHGTCM | Plant height (cm) at end of flowering. Plant height was measured with a measuring tape. The value reported corresponds to the plant height from its base to the tallest branch. |
| Pod Ripening Class | Maturity rating for pod ripening in the field. |
| PROTEINPCT | Seed protein % via ARV NIR. Approximately 1 gram of mature seed was placed in an individual clear glass vial for NIR analysis. |
| SEED1000 | 1000 seed weight in grams. The weight reported was measured with an automatic seed counter. |
| SEEDCOLOR | Seed color at harvest |
| Seeds Per Pod | Seeds per pod averaged over 5 pods taken from the main flower stem. The value reported was done by selecting 10 unopen pods from the center of the main stem. Pods were manually opened and seeds were counted from each individual plant. |
| SINIGRIN | Sinigrin in micromoles per gram as measured via NIR. Approximately 1 gram of mature seed was placed in an individual clear glass vial for NIR analysis. |
| Stem Anthocyanin | Verbal rendition of stem anthocyanin during peak flowering. Visual observation of the level of Anthocyanin present on the main stem. |
| Stem anthocyanin rating | Level of stem anthocyanin: 1 = absent. 2 = weak, 3 = medium, 4 = strong/ |
| Stem Diameter | Stem diameter of main stem in mm. The stem diameter was measured with a digital caliper. The stem diameter was measured at 10 cm from the base of the main stem. |

Further Embodiments

The disclosure provides methods and compositions relating to plants, seeds and derivatives of a new pennycress variety herein referred to as pennycress variety B3.

There are numerous steps in the development of any novel plant with desirable characteristics. Selection of traits is a very important aspect of plant breeding. Once desirable traits are identified, the plants with those desirable traits are crossed in order to recombine the desirable traits and through selection, varieties or parent lines are developed.

Choice of breeding or selection methods depends on the mode of plant reproduction, the heritability of the trait(s) being improved, and the type of variety used commercially (e.g., F1 hybrid, pureline, etc.). Popular selection methods commonly include but are not limited to pedigree selection, modified pedigree selection, mass selection, and recurrent selection.

The complexity of inheritance influences choice of the breeding method. Backcross breeding is used to transfer one or a few favorable genes for a highly heritable trait into a desirable variety. This approach is used extensively for breeding, for example, disease-resistant varieties. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Pedigree breeding is used commonly for the improvement of self-pollinating crops or inbred lines of cross-pollinating crops. Two parents which possess favorable, complementary traits are crossed to produce an F1. An F2 population is produced by selfing one or several F1s or by intercrossing two F1s (sib mating). Selection of the best individuals is usually begun in the F2 population; then, beginning in the F3, the best individuals in the best families are selected. Replicated testing of families, or hybrid combinations involving individuals of these families, often follows in the F4 generation to improve the effectiveness of selection for traits with low heritability. At an advanced stage of inbreeding (i.e., F6 and F7), the best lines or mixtures of phenotypically similar lines are tested for potential release as new varieties.

Mass and recurrent selections may be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Backcross breeding has been used to transfer genes for a simply inherited, highly heritable trait into a desirable homozygous variety or line that is the recurrent parent. The source of the trait to be transferred is called the donor parent. The resulting plant is expected to have the attributes of the recurrent parent (e.g., variety) and the desirable trait transferred from the donor parent. After the initial cross, individuals possessing the phenotype of the donor parent are selected and repeatedly crossed (backcrossed) to the recurrent parent. The resulting plant is expected to have the attributes of the recurrent parent (e.g., variety) and the desirable trait transferred from the donor parent.

Other methods of breeding may also relate to the single-seed descent procedure which refers to planting a segregating population, harvesting a sample of one seed per plant, and using the one-seed sample to plant the next generation. When the population has been advanced from the F2 to the desired level of inbreeding, the plants from which lines are derived will each trace to different F2 individuals. The number of plants in a population declines each generation due to failure of some seeds to germinate or some plants to produce at least one seed. As a result, not all of the F2 plants originally sampled in the population will be represented by a progeny when generation advance is completed.

In addition to phenotypic observations, the genotype of a plant may also be examined. There are many laboratory-based techniques available for the analysis, comparison and characterization of plant genotype; these techniques include but are not limited to Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length polymorphisms (AFLPs), Simple Sequence Repeats (SSRs—which are also referred to as Microsatellites), and Single Nucleotide Polymorphisms (SNPs).

Isozyme Electrophoresis and RFLPs have been widely used to determine genetic composition. SSR technology is currently the most efficient and practical marker technology; more marker loci may be routinely used and more alleles per marker locus may be found using SSRs in comparison to RFLPs. SNPs may also be used to identify the unique genetic composition of the disclosure and progeny varieties retaining that unique genetic composition. Various molecular marker techniques may be used in combination to enhance overall resolution.

Molecular markers, which include markers identified through the use of techniques such as Isozyme Electrophoresis, RFLPs, RAPDs, AP-PCR, DAF, SCARs, AFLPs, SSRs, and SNPs, may be used in plant breeding. One use of molecular markers is Quantitative Trait Loci (QTL) mapping. QTL mapping is the use of markers which are known to be closely linked to alleles that have measurable effects on a quantitative trait. Selection in the breeding process is based upon the accumulation of markers linked to the positive effecting alleles and/or the elimination of the markers linked to the negative effecting alleles from the plant's genome.

Molecular markers may also be used during the breeding process for the selection of qualitative traits. For example, markers closely linked to alleles or markers containing sequences within the actual alleles of interest may be used to select plants that contain the alleles of interest during a backcrossing breeding program. The markers may also be used to select toward the genome of the recurrent parent and against the markers of the donor parent. This procedure attempts to minimize the amount of genome from the donor parent that remains in the selected plants. It may also be used to reduce the number of crosses back to the recurrent parent needed in a backcrossing program. The use of molecular markers in the selection process is often called genetic marker enhanced selection or marker-assisted selection. Molecular markers may also be used to identify and exclude certain sources of germplasm as parental varieties or ancestors of a plant by providing a means of tracking genetic profiles through crosses.

Mutation breeding is another method of introducing new traits into pennycress varieties. Mutations that occur spontaneously or are artificially induced may be useful sources of variability for a plant breeder. The goal of artificial mutagenesis is to increase the rate of mutation for a desired characteristic. Mutation rates may be increased by many different means including temperature, long-term seed storage, tissue culture conditions, radiation (such as X-rays, Gamma rays, neutrons, Beta radiation, or ultraviolet radiation), chemical mutagens (such as base analogs like 5-bromo-uracil), antibiotics, alkylating agents (such as sulfur mustards, nitrogen mustards, epoxides, ethyleneamines, sulfates, sulfonates, sulfones, or lactones), azide, hydroxylamine, nitrous acid or acridines. Once a desired trait is observed through mutagenesis the trait may then be incorporated into existing germplasm by traditional breeding techniques. Details of mutation breeding may be found in Principles of Cultivar Development by Fehr, Macmillan Publishing Company, 1993.

The production of double haploids may also be used for the development of homozygous lines in a breeding program. Double haploids are produced by the doubling of a set of chromosomes from a heterozygous plant to produce a completely homozygous individual. For example, see Wan et al., Theor. Appl. Genet., 77:889-892, 1989.

Descriptions of other breeding methods that are commonly used for different traits and crops can be found in one of several reference books (e.g., Principles of Plant Breeding John Wiley and Son, pp. 115-161, 1960; Allard, 1960; Simmonds, 1979; Sneep et al., 1979; Fehr, 1987; "Carrots and Related Vegetable Umbelliferae", Rubatzky, V. E., et al., 1999).

Descriptions of other breeding methods that are commonly used for different traits and crops can be found in one of several reference books (e.g., Principles of Plant Breeding John Wiley and Son, pp. 115-161, 1960; Allard, 1960; Simmonds, 1979; Sneep et al., 1979; Fehr, 1987; "Carrots and Related Vegetable Umbelliferae", Rubatzky, V. E., et al., 1999).

Pennycress is an important and valuable crop. Pennycress has value in both its oil and the resulting meal following the removal of oil. The meal is used for animal feed and is typically valued for its energy, protein and sometimes fiber. Thus, a continuing goal of pennycress plant breeders is to develop stable, high yielding pennycress varieties that are agronomically sound. To accomplish this goal, the pennycress breeder preferably selects and develops pennycress plants with traits that result in superior varieties.

This disclosure also is directed to methods for producing a pennycress plant by crossing a first parent pennycress plant with a second parent pennycress plant wherein either the first or second parent pennycress plant is a pennycress plant of the variety B3. Further, both first and second parent pennycress plants can come from the variety B3. Still further, this disclosure also is directed to methods for producing a B3-derived pennycress plant by crossing variety B3 with a second pennycress plant and growing the progeny seed and repeating the crossing and growing steps with the B3-derived plant from 0 to 7 times. Thus, any such methods using the variety B3 are part of this disclosure: selfing, backcrosses, hybrid production, crosses to populations, and the like. All plants produced using variety B3 as a parent are within the scope of this disclosure, including plants derived from variety B3. Advantageously, the variety may be used in crosses with other, different, varieties to produce first generation ($F_1$) pennycress seeds and plants with superior characteristics.

The advent of new molecular biological techniques has allowed the isolation and characterization of genetic elements with specific functions, such as encoding specific protein products. Scientists in the field of plant biology developed a strong interest in engineering the genome of plants to contain and express foreign genetic elements, or additional, or modified versions of native or endogenous genetic elements in order to alter the traits of a plant in a specific manner. In some embodiments, a transgenic variant of pennycress variety B3 may contain at least one transgene but could contain at least 1, 2, 3, 4, 5, 6, 7, 8, 9, 10, and/or no more than 15, 14, 13, 12, 11, 10, 9, 8, 7, 6, 5, 4, 3, or 2. Over the last 15 to 20 years several methods for producing transgenic plants have been developed, and the present disclosure also relates to transgenic variants of pennycress variety B3.

Nucleic acids or polynucleotides refer to RNA or DNA that is linear or branched, single or double stranded, or a hybrid thereof. The term also encompasses RNA/DNA hybrids. These terms also encompass untranslated sequence located at both the 3' and 5' ends of the coding region of the gene: at least approximately 1000 nucleotides of sequence upstream from the 5' end of the coding region and at least approximately 200 nucleotides of sequence downstream from the 3' end of the coding region of the gene. Less common bases, such as inosine, 5-methylcytosine, 6-methyladenine, hypoxanthine and others can also be used for antisense, dsRNA and ribozyme pairing. For example, polynucleotides that contain C-5 propyne analogues of uridine and cytidine have been shown to bind RNA with high affinity and to be potent antisense inhibitors of gene expression. Other modifications, such as modification to the phosphodiester backbone, or the 2'-hydroxy in the ribose sugar group of the RNA can also be made. The antisense polynucleotides and ribozymes can consist entirely of ribonucleotides, or can contain mixed ribonucleotides and deoxyribonucleotides. The polynucleotides of the disclosure may be produced by any means, including genomic preparations, cDNA preparations, in vitro synthesis, RT-PCR, and in vitro or in vivo transcription.

One embodiment of the disclosure is a process for producing pennycress variety B3 further comprising a desired trait, the process comprising introducing a transgene that confers a desired trait to a pennycress plant of variety B3. Another embodiment is the product produced by this process. In one embodiment, the desired trait may be one or more of herbicide resistance, insect resistance, disease resistance, male sterility, reduced seed fiber content, modified seed color, earlier maturity, increased or modified seed protein composition, increased or modified seed oil or fatty acid content, reduced seed glucosinolate content, or shatter resistance. The specific gene may be any known in the art or listed herein.

Numerous methods for plant transformation have been developed, including biological and physical plant transformation protocols. See, for example, Miki et al., "Procedures for Introducing Foreign DNA into Plants," in *Methods in Plant Molecular Biology and Biotechnology*, Glick and Thompson Eds., CRC Press, Inc., Boca Raton, pp. 67-88 (1993), and Armstrong, "The First Decade of Maize Transformation: A Review and Future Perspective," *Maydica*, 44:101-109 (1999). In addition, expression vectors and in vitro culture methods for plant cell or tissue transformation and regeneration of plants are available. See, for example, Gruber et al., "Vectors for Plant Transformation," in *Methods in Plant Molecular Biology and Biotechnology*, Glick and Thompson Eds., CRC Press, Inc., Boca Raton, pp. 89-119 (1993).

A genetic trait which has been engineered into the genome of a particular pennycress plant may then be moved into the genome of another variety using traditional breeding techniques that are well known in the plant breeding arts. For example, a backcrossing approach is used to move a transgene from a transformed pennycress variety into an already developed pennycress variety, and the resulting backcross conversion plant would then comprise the transgene(s).

Various genetic elements can be introduced into the plant genome using transformation. These elements include, but are not limited to, genes, coding sequences, inducible, constitutive and tissue specific promoters, enhancing sequences, and signal and targeting sequences. For example, see the traits, genes, and transformation methods listed in U.S. Pat. No. 6,118,055.

Included among various plant transformation techniques are methods that permit the site-specific modification of a plant genome, including coding sequences, regulatory elements, non-coding and other DNA sequences in a plant genome. Such methods are well-known in the art and include, for example, use of the CRISPR-Cas system, zinc-finger nucleases (ZFNs), and transcription activator-like effector nucleases (TALENs), among others.

Expression Vectors

Plant transformation may involve the construction of an expression vector which will function in plant cells. Such a vector can comprise DNA comprising a gene under control of, or operatively linked to, a regulatory element (for example, a promoter). The expression vector may contain one or more such operably linked gene/regulatory element combinations. The vector(s) may be in the form of a plasmid and can be used alone or in combination with other plasmids to provide transformed pennycress plants using transformation methods as described below to incorporate transgenes into the genetic material of the pennycress plant(s).

Expression vectors include at least one genetic marker operably linked to a regulatory element (for example, a promoter) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well known in the transformation arts, and include, for example, genes that code for enzymes that metabolically detoxify a selective chemical agent which may be an antibiotic or an herbicide, or genes that encode an altered target which is insensitive to the inhibitor. A few positive selection methods are also known in the art.

One commonly used selectable marker gene for plant transformation is the neomycin phosphotransferase II (nptII) gene which, when under the control of plant regulatory signals, confers resistance to kanamycin. Fraley et al., *Proc. Natl. Acad. Sci. USA,* 80:4803 (1983). Another commonly used selectable marker gene is the hygromycin phosphotransferase gene which confers resistance to the antibiotic hygromycin. Vanden Elzen et al., *Plant Mol. Biol.,* 5:299 (1985).

Additional selectable marker genes of bacterial origin that confer resistance to antibiotics include gentamycin acetyl transferase, streptomycin phosphotransferase and aminoglycoside-3'-adenyl transferase, the bleomycin resistance determinant (Hayford et al., *Plant Physiol.,* 86:1216 (1988); Jones et al., *Mol. Gen. Genet.,* 210:86 (1987); Svab et al., *Plant Mol. Biol.,* 14:197 (1990); Hille et al., *Plant Mol. Biol.,* 7:171 (1986)). Other selectable marker genes confer resistance to herbicides such as glyphosate, glufosinate, or bromoxynil (Comai et al., *Nature,* 317:741-744 (1985); Gordon-Kamm et al., *Plant Cell,* 2:603-618 (1990); Stalke et al., *Science,* 242:419-423 (1988)).

Selectable marker genes for plant transformation not of bacterial origin include, for example, mouse dihydrofolate reductase, plant 5-enolpyruvylshikimate-3-phosphate synthase, and plant acetolactate synthase (Eichholtz et al., *Somatic Cell Mol. Genet.,* 13:67 (1987); Shah et al., *Science,* 233:478 (1986); Charest et al., *Plant Cell Rep.,* 8:643 (1990)).

Another class of marker genes for plant transformation requires screening of presumptively transformed plant cells, rather than direct genetic selection of transformed cells, for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include β-glucuronidase (GUS), β-galactosidase, luciferase, and chloramphenicol acetyltransferase (Jefferson, R. A., *Plant Mol. Biol. Rep.,* 5:387 (1987); Teeri et al., *EMBO J.,* 8:343 (1989);

Koncz et al., *Proc. Natl. Acad. Sci. USA,* 84:131 (1987); DeBlock et al., *EMBO J.,* 3:1681 (1984)).

In vivo methods for visualizing GUS activity that do not require destruction of plant tissue are available (Molecular Probes, Publication 2908, IMAGENE GREEN, pp. 1-4 (1993); Naleway et al., *J. Cell Biol.,* 115: 151a (1991)). However, these in vivo methods for visualizing GUS activity have not proven useful for recovery of transformed cells because of low sensitivity, high fluorescent backgrounds, and limitations associated with the use of luciferase genes as selectable markers.

More recently, a gene encoding Green Fluorescent Protein (GFP) has been utilized as a marker for gene expression in prokaryotic and eukaryotic cells (Chalfie et al., *Science,* 263:802 (1994)). GFP and mutants of GFP may be used as screenable markers.

Genes included in expression vectors must be driven by a nucleotide sequence comprising a regulatory element (for example, a promoter). Several types of promoters are well known in the transformation arts as are other regulatory elements that can be used alone or in combination with promoters.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred." Promoters that initiate transcription only in a certain tissue are referred to as "tissue-specific." A "cell-type" specific promoter primarily drives expression in certain cell types in one or more organs, for example, vascular cells in roots or leaves. An "inducible" promoter is a promoter which is under environmental control. Examples of environmental conditions that may affect transcription by inducible promoters include anaerobic conditions or the presence of light. Tissue-specific, tissue-preferred, cell-type specific, and inducible promoters constitute the class of "non-constitutive" promoters. A "constitutive" promoter is a promoter that is active under most environmental conditions.

A. Inducible Promoters—An inducible promoter is operably linked to a gene for expression in pennycress. Optionally, the inducible promoter is operably linked to a nucleotide sequence encoding a signal sequence which is operably linked to a gene for expression in pennycress. With an inducible promoter the rate of transcription increases in response to an inducing agent.

Any inducible promoter can be used. See, Ward et al., *Plant Mol. Biol.,* 22:361-366 (1993). Exemplary inducible promoters include, but are not limited to, that from the ACEI system which responds to copper (Mett et al., *Proc. Natl. Acad. Sci. USA,* 90:4567-4571 (1993)); In2 gene from maize which responds to benzenesulfonamide herbicide safeners (Hershey et al., *Mol. Gen Genetics,* 227:229-237 (1991); Gatz et al., *Mol. Gen. Genetics,* 243:32-38 (1994)); or Tet repressor from Tn10 (Gatz et al., *Mol. Gen. Genetics,* 227:229-237 (1991)). A particularly preferred inducible promoter is a promoter that responds to an inducing agent to which plants do not normally respond. An exemplary inducible promoter is the inducible promoter from a steroid hormone gene, glucocorticoid response elements, the transcriptional activity of which is induced by a glucocorticoid hormone (Schena et al., *Proc. Natl. Acad. Sci. USA*, 88:10421-10425 (1991)).

B. Constitutive Promoters—A constitutive promoter is operably linked to a gene for expression in pennycress or the constitutive promoter is operably linked to a nucleotide sequence encoding a signal sequence which is operably linked to a gene for expression in pennycress.

Many different constitutive promoters can be utilized. Exemplary constitutive promoters include, but are not limited to, the promoters from plant viruses such as the 35S promoter from CaMV (Odell et al., *Nature*, 313:810-812 (1985)) and the promoters from such genes as rice actin (McElroy et al., *Plant Cell*, 2:163-171 (1990)); ubiquitin (Christensen et al., *Plant Mol. Biol.*, 12:619-632 (1989); Christensen et al., *Plant Mol. Biol.*, 18:675-689 (1992)); pEMU (Last et al., *Theor. Appl. Genet.*, 81:581-588 (1991)); MAS (Velten et al., *EMBO J.*, 3:2723-2730 (1984)); and maize H3 histone (Lepetit et al., *Mol. Gen. Genetics*, 231: 276-285 (1992); Atanassova et al., *Plant Journal*, 2 (3): 291-300 (1992)). The ALS promoter, an Xbal/Ncol fragment 5' to the *Brassica napus* ALS3 structural gene (or a nucleotide sequence similarity to said Xbal/Ncol fragment), represents a particularly useful constitutive promoter. See PCT Application WO 96/30530.

C. Tissue-Specific or Tissue-Preferred Promoters—A tissue-specific promoter is operably linked to a gene for expression in pennycress. Optionally, the tissue-specific promoter is operably linked to a nucleotide sequence encoding a signal sequence which is operably linked to a gene for expression in pennycress. Plants transformed with a gene of interest operably linked to a tissue-specific promoter produce the protein product of the transgene exclusively, or preferentially, in a specific tissue.

Any tissue-specific or tissue-preferred promoter can be utilized. Exemplary tissue-specific or tissue-preferred promoters include, but are not limited to, a root-preferred promoter such as that from the phaseolin gene (Murai et al., Science, 23:476-482 (1983); Sengupta-Gopalan et al., *Proc. Natl. Acad. Sci. USA*, 82:3320-3324 (1985)); a leaf-specific and light-induced promoter such as that from cab or rubisco (Simpson et al., *EMBO J.*, 4(11):2723-2729 (1985); Timko et al., *Nature*, 318:579-582 (1985)); an anther-specific promoter such as that from LAT52 (Twell et al., *Mol. Gen. Genetics*, 217:240-245 (1989)); a pollen-specific promoter such as that from Zm13 (Guerrero et al., *Mol. Gen. Genetics*, 244:161-168 (1993)); or a microspore-preferred promoter such as that from apg (Twell et al., *Sex. Plant Reprod.*, 6:217-224 (1993)).

Transport of a protein produced by transgenes to a subcellular compartment, such as the chloroplast, vacuole, peroxisome, glyoxysome, cell wall, or mitochondrion, or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine during protein synthesis and processing where the encoded protein is ultimately compartmentalized.

The presence of a signal sequence directs a polypeptide to either an intracellular organelle or subcellular compartment or for secretion to the apoplast. Many signal sequences are known in the art. See, for example, Becker et al., *Plant Mol. Biol.*, 20:49 (1992); Knox, C. et al., *Plant Mol. Biol.*, 9:3-17 (1987); Lerner et al., *Plant Physiol.*, 91:124-129 (1989); Frontes et al., *Plant Cell*, 3:483-496 (1991); Matsuoka et al., *Proc. Natl. Acad. Sci.*, 88:834 (1991); Gould et al., *J. Cell.*

*Biol.*, 108:1657 (1989); Creissen et al., *Plant J.*, 2:129 (1991); Kalderon et al., *Cell*, 39:499-509 (1984); Steifel et al., *Plant Cell*, 2:785-793 (1990).

Agronomic Genes

By means of the present disclosure, pennycress plants can be genetically engineered or modified to express various phenotypes of agronomic interest. Through the transformation of pennycress, the expression of genes can be altered to enhance disease resistance, insect resistance, herbicide resistance, agronomic, grain quality, and other traits. DNA sequences native to pennycress, as well as non-native DNA sequences, can be transformed into pennycress and used to alter levels of native or non-native proteins. Various promoters, targeting sequences, enhancing sequences, and other DNA sequences can be inserted into the genome for the purpose of altering the expression of proteins. Reduction of the expression or activity of specific genes is desirable for several aspects of genetic engineering in plants. Suppression of endogenous pennycress gene expression can be affected by a variety of techniques including, but not limited to, loss-of-function mutations in endogenous genes, with transgenes, or by using gene-editing or mutagenesis-mediated genome rearrangements.

Many techniques for gene silencing are well known to one of skill in the art, including, but not limited to, knock-outs (such as by insertion of a transposable element such as mu (Vicki Chandler, The Maize Handbook, Ch. 118 (Springer-Verlag 1994)) or other genetic elements such as a FRT and Lox that are used for site specific integrations, antisense technology (see, e.g., Sheehy et al., *PNAS USA*, 85:8805-8809 (1988); and U.S. Pat. Nos. 5,107,065, 5,453,566, and 5,759,829); co-suppression (e.g., Taylor, *Plant Cell*, 9:1245 (1997); Jorgensen, *Trends Biotech.*, 8(12):340-344 (1990); Flavell, *PNAS USA*, 91:3490-3496 (1994); Finnegan et al., *Bio/Technology*, 12:883-888 (1994); Neuhuber et al., *Mol. Gen. Genet.*, 244:230-241 (1994)); RNA interference (Napoli et al., *Plant Cell*, 2:279-289 (1990); U.S. Pat. No. 5,034,323; Sharp, *Genes Dev.*, 13:139-141 (1999); Zamore et al., *Cell*, 101:25-33 (2000); Montgomery et al., *PNAS USA*, 95:15502-15507 (1998)), virus-induced gene silencing (Burton et al., *Plant Cell*, 12:691-705 (2000); Baulcombe, *Curr. Op. Plant Bio.*, 2:109-113 (1999)); target-RNA-specific ribozymes (Haseloff et al., *Nature*, 334:585-591 (1988)); hairpin structures (Smith et al., *Nature*, 407:319-320 (2000); WO 99/53050; WO 98/53083); MicroRNA (Aukerman & Sakai, *Plant Cell*, 15:2730-2741 (2003)); ribozymes (Steinecke et al., *EMBO J.*, 11:1525 (1992); Perriman et al., *Antisense Res. Dev.*, 3:253 (1993)); oligonucleotide mediated targeted modification (e.g., WO 03/076574 and WO 99/25853); Zn-finger targeted molecules (e.g., WO 01/52620, WO 03/048345, and WO 00/42219); and other methods or combinations of the above methods known to those of skill in the art.

Exemplary transgenes or modified genes include, but are not limited to, those categorized below:

1. Genes that confer resistance to pests or disease and that encode:

(A) Plant disease resistance genes. Plant defenses are often activated by specific interaction between the product of a disease resistance gene (R) in the plant and the product of a corresponding avirulence (Avr) gene in the pathogen. A plant variety can be transformed with one or more cloned resistance genes to engineer plants that are resistant to specific pathogen strains. See, for example, Jones et al., Science, 266:789 (1994) (cloning of the tomato Cf-9 gene for resistance to *Cladosporium flavum*); Martin et al., *Science*, 262:1432 (1993) (tomato Pto gene for resistance to *Pseudomonas syringae* pv. tomato encodes a protein kinase); Mindrinos et al., *Cell,* 78:1089 (1994) (*Arabidopsis* RSP2 gene for resistance to *Pseudomonas syringae*); McDowell & Woffenden, *Trends Biotechnol.,* 21(4):178-83 (2003); and Toyoda et al., *Transgenic Res.,* 11 (6):567-82 (2002).

(B) A *Bacillus thuringiensis* protein, a derivative thereof or a synthetic polypeptide modelled thereon. See, for example, Geiser et al., *Gene,* 48:109 (1986), who disclose the cloning and nucleotide sequence of a Bt δ-endotoxin gene. Moreover, DNA molecules encoding δ-endotoxin genes can be purchased from American Type Culture Collection, Manassas, Va., for example, under ATCC Accession Nos. 40098, 67136, 31995, and 31998.

(C) A lectin. See, for example, Van Damme et al., *Plant Molec. Biol.,* 24:25 (1994), who disclose the nucleotide sequences of several *Clivia miniata* mannose-binding lectin genes.

(D) A vitamin-binding protein such as avidin. See, PCT Application US 93/06487, which teaches the use of avidin and avidin homologues as larvicides against insect pests.

(E) An enzyme inhibitor, for example, a protease or proteinase inhibitor or an amylase inhibitor. See, for example, Abe et al., *J. Biol. Chem.,* 262:16793 (1987) (nucleotide sequence of rice cysteine proteinase inhibitor); Huub et al., *Plant Molec. Biol.,* 21:985 (1993) (nucleotide sequence of cDNA encoding tobacco proteinase inhibitor I); Sumitani et al., Biosci. Biotech. Biochem., 57:1243 (1993) (nucleotide sequence of *Streptomyces nitrosporeus* α-amylase inhibitor); and U.S. Pat. No. 5,494,813 (Hepher and Atkinson, issued Feb. 27, 1996).

(F) An insect-specific hormone or pheromone, such as an ecdysteroid or juvenile hormone, a variant thereof, a mimetic based thereon, or an antagonist or agonist thereof. See, for example, the disclosure by Hammock et al., *Nature,* 344:458 (1990), of baculovirus expression of cloned juvenile hormone esterase, an inactivator of juvenile hormone.

(G) An insect-specific peptide or neuropeptide which, upon expression, disrupts the physiology of the affected pest. For example, see the disclosures of Regan, *J. Biol. Chem.,* 269:9 (1994) (expression cloning yields DNA coding for insect diuretic hormone receptor); Pratt et al., *Biochem. Biophys. Res. Comm.,* 163:1243 (1989) (an allostatin is identified in *Diploptera puntata*); Chattopadhyay et al., *Critical Reviews in Microbiology,* 30(1):33-54 (2004); Zjawiony, *J Nat Prod,* 67(2):300-310 (2004); Carlini & Grossi-de-Sa, *Toxicon,* 40(11): 1515-1539 (2002); Ussuf et al., *Curr Sci.,* 80(7):847-853 (2001); Vasconcelos & Oliveira, *Toxicon,* 44(4): 385-403 (2004). See also, U.S. Pat. No. 5,266,317 to Tomalski et al., which discloses genes encoding insect-specific, paralytic neurotoxins.

(H) An insect-specific venom produced in nature by a snake, a wasp, etc. For example, see, Pang et al., *Gene,* 116:165 (1992), for disclosure of heterologous expression in plants of a gene coding for a scorpion insectotoxic peptide.

(I) An enzyme responsible for a hyperaccumulation of a monoterpene, a sesquiterpene, a steroid, hydroxamic acid, a phenylpropanoid derivative, or another non-protein molecule with insecticidal activity.

(J) An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase, and a glucanase, whether natural or synthetic. See, PCT Application WO 93/02197 (Scott et al.), which discloses the nucleotide sequence of a callase gene. DNA molecules which contain chitinase-encoding sequences can be obtained, for example, from the ATCC under Accession Nos. 39637 and 67152. See also, Kramer et al., Insect Biochem. Molec. Biol., 23:691 (1993), who teach the nucleotide sequence of a cDNA encoding tobacco hornworm chitinase, and Kawalleck et al., *Plant Molec. Biol.,* 21:673 (1993), who provide the nucleotide sequence of the parsley ubi4-2 polyubiquitin gene, U.S. Pat. Nos. 7,145,060, 7,087,810, and 6,563,020.

(K) A molecule that stimulates signal transduction. For example, see the disclosure by Botella et al., *Plant Molec. Biol.,* 24:757 (1994), of nucleotide sequences for mung bean calmodulin cDNA clones, and Griess et al., *Plant Physiol.,* 104:1467 (1994), who provide the nucleotide sequence of a maize calmodulin cDNA clone.

(L) A hydrophobic moment peptide. See, PCT Application WO 95/16776 and U.S. Pat. No. 5,580,852, which disclose peptide derivatives of tachyplesin which inhibit fungal plant pathogens, and PCT Application WO 95/18855 and U.S. Pat. No. 5,607,914 which teaches synthetic antimicrobial peptides that confer disease resistance.

(M) A membrane permease, a channel former or a channel blocker. For example, see the disclosure of Jaynes et al., *Plant Sci,* 89:43 (1993), of heterologous expression of a cecropin-β lytic peptide analog to render transgenic tobacco plants resistant to *Pseudomonas solanacearum.*

(N) A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See, Beachy et al., *Ann. Rev. Phytopathol.,* 28:451 (1990). Coat protein-mediated resistance has been conferred upon transformed plants against alfalfa mosaic virus, cucumber mosaic virus, and tobacco mosaic virus.

(O) An insect-specific antibody or an immunotoxin derived therefrom. Thus, an antibody targeted to a critical metabolic function in the insect gut would inactivate an affected enzyme, killing the insect. See, Taylor et al., Abstract #497, Seventh Int'l Symposium on Molecular Plant-Microbe Interactions (Edinburgh, Scotland 1994) (enzymatic inactivation in transgenic tobacco via production of single-chain antibody fragments).

(P) A virus-specific antibody. See, for example, Tavladoraki et al., *Nature,* 366:469 (1993), who show that transgenic plants expressing recombinant antibody genes are protected from virus attack.

(Q) A developmental-arrestive protein produced in nature by a pathogen or a parasite. Thus, fungal endo-α-1, 4-D-polygalacturonases facilitate fungal colonization and plant nutrient release by solubilizing plant cell wall homo-α-1,4-D-galacturonase. See, Lamb et al., *Bio/ Technology,* 10:1436 (1992). The cloning and characterization of a gene which encodes a bean endopolygalacturonase-inhibiting protein is described by Toubart et al., *Plant J.,* 2:367 (1992).

(R) A developmental-arrestive protein produced in nature by a plant. For example, Logemann et al., Bio/Technology, 10:305 (1992), have shown that transgenic plants expressing the barley ribosome-inactivating gene have an increased resistance to fungal disease.

(S) Genes involved in the Systemic Acquired Resistance (SAR) Response and/or the pathogenesis-related genes. Briggs, S., *Current Biology,* 5(2) (1995); Pieterse & Van Loon, *Curr. Opin. Plant Bio.,* 7(4):456-64 (2004); and Somssich, *Cell,* 113 (7):815-6 (2003).

(T) Antifungal genes. See, Cornelissen and Melchers, *Plant Physiol.,* 101:709-712 (1993); Parijs et al., *Planta,* 183:258-264 (1991); and Bushnell et al., *Can. J. of Plant Path.,* 20(2):137-149 (1998). See also, U.S. Pat. No. 6,875,907.

(U) Cystatin and cysteine proteinase inhibitors. See, U.S. Pat. No. 7,205,453.

(V) Defensin genes. See, WO 03/000863 and U.S. Pat. No. 6,911,577.

Any of the above-listed disease or pest resistance genes can be introduced into the claimed pennycress variety through a variety of means including, but not limited to, transformation and crossing.

2. Genes that confer resistance to an herbicide, for example:

(A) An herbicide that inhibits the growing point or meristem, such as an imidazolinone or a sulfonylurea. Exemplary genes in this category code for mutant ALS and AHAS enzyme as described, for example, by Lee et al., *EMBO J.,* 7:1241 (1988) and Miki et al., *Theor. Appl. Genet.,* 80:449 (1990), respectively.

(B) Glyphosate (resistance conferred by mutant 5-enolpyruvlshikimate-3-phosphate synthase (EPSPS) and aroA genes, respectively) and other phosphono compounds, such as glufosinate (phosphinothricin acetyl transferase (PAT) and *Streptomyces hygroscopicus* PAT bar genes), pyridinoxy or phenoxy propionic acids, and cyclohexanediones (ACCase inhibitor-encoding genes). See, for example, U.S. Pat. No. 4,940, 835 to Shah et al., which discloses the nucleotide sequence of a form of EPSPS which can confer glyphosate resistance. U.S. Pat. No. 5,627,061 to Barry et al., also describes genes encoding EPSPS enzymes. See also, U.S. Pat. Nos. 6,566,587, 6,338,961, 6,248,876, 6,040,497, 5,804,425, 5,633,435, 5,145,783, 4,971, 908, 5,312,910, 5,188,642, 4,940,835, 5,866,775, 6,225,114, 6,130,366, 5,310,667, 4,535,060, 4,769, 061, 5,633,448, 5,510,471, RE 36,449, RE 37,287, and 5,491,288; and International Publications EP1173580, WO 01/66704, EP1173581, and EP1173582, which are incorporated herein by reference for this purpose. Glyphosate resistance is also imparted to plants that express a gene that encodes a glyphosate oxido-reductase enzyme, as described more fully in U.S. Pat. Nos. 5,776,760 and 5,463,175, which are incorporated herein by reference for this purpose. In addition, glyphosate resistance can be imparted to plants by the over expression of genes encoding glyphosate N-acetyl-transferase. See, for example, U.S. Pat. No. 7,462,481. A DNA molecule encoding a mutant aroA gene can be obtained under ATCC Accession No. 39256, and the nucleotide sequence of the mutant gene is disclosed in U.S. Pat. No. 4,769,061 to Comai. European Patent Appl. No. 0 333 033 to Kumada et al. and U.S. Pat. No. 4,975,374 to Goodman et al., disclose nucleotide sequences of glutamine synthetase genes which confer resistance to herbicides such as L-phosphinothricin. The nucleotide sequence of a PAT gene is provided in European Patent Appl. No. 0 242 246 to Leemans et al. DeGree F. et al., *Bio/Technology,* 7:61 (1989) describe the production of transgenic plants that express chimeric bar genes coding for phosphinothricin acetyl transferase activity. Exemplary of genes conferring resistance to phenoxy propionic acids and cyclohexanediones, such as sethoxydim and haloxyfop are the Acc1-S1, Acc1-S2, and Acc2-S3 genes described by Marshall et al., *Theor. Appl. Genet.,* 83:435 (1992).

(C) An herbicide that inhibits photosynthesis, such as a triazine (psbA and gs+ genes) and a benzonitrile (nitrilase gene). Przibila et al., *Plant Cell,* 3:169 (1991), describe the transformation of *Chlamydomonas* with plasmids encoding mutant psbA genes. Nucleotide sequences for nitrilase genes are disclosed in U.S. Pat. No. 4,810,648 to Stalker and DNA molecules containing these genes are available under ATCC Accession Nos. 53435, 67441, and 67442. Cloning and expression of DNA coding for a glutathione S-transferase is described by Hayes et al., *Biochem. J.,* 285:173 (1992).

(D) Acetohydroxy acid synthase, which has been found to make plants that express this enzyme resistant to multiple types of herbicides, has been introduced into a variety of plants. See, Hattori et al., *Mol. Gen. Genet.,* 246:419 (1995). Other genes that confer tolerance to herbicides include a gene encoding a chimeric protein of rat cytochrome P4507A1 and yeast NADPH-cytochrome P450 oxidoreductase (Shiota et al., *Plant Physiol.,* 106:17 (1994)); genes for glutathione reductase and superoxide dismutase (Aono et al., *Plant Cell Physiol.,* 36:1687 (1995)); and genes for various phosphotransferases (Datta et al., *Plant Mol. Biol.,* 20:619 (1992)).

(E) Protoporphyrinogen oxidase (protox) is necessary for the production of chlorophyll, which is necessary for all plant survival. The protox enzyme serves as the target for a variety of herbicidal compounds. These herbicides also inhibit growth of all the different species of plants present, causing their total destruction. The development of plants containing altered protox activity which are resistant to these herbicides are described in U.S. Pat. Nos. 6,288,306, 6,282,837, 5,767,373, and International Publication WO 01/12825.

(F) 4-hydroxyphenylpyruvate dioxygenase (HPPD) is a target of the HPPD-inhibiting herbicides. Inhibition of HPPD leads to uncoupling of photosynthesis, deficiency in accessory light-harvesting pigments and to destruction of chlorophyll by UV-radiation and reactive oxygen species due to the lack of photo protection normally provided by carotenoids. Photo bleaching of photosynthetically active tissues leads to growth inhibition and plant death. Plants can be transformed with a gene encoding a naturally-occurring resistant HPPD enzyme, or a gene encoding a mutated or chimeric HPPD enzyme as described in WO 96/38567, WO 99/24585, WO 99/24586, WO 09/144079, WO 02/046387, or U.S. Pat. No. 6,768,044. Tolerance to HPPD-inhibitors can also be obtained by transforming plants with genes encoding certain enzymes enabling the formation of homogentisate despite the inhibition of the native HPPD enzyme by the HPPD-inhibitor. Such plants and genes are described in WO 99/34008 and WO 02/36787. Tolerance of plants to HPPD inhibitors can also be improved by transforming plants with a gene encoding an enzyme having prephenate deshy-drogenase (PDH) activity in addition to a gene encoding an HPPD-tolerant enzyme, as described in WO 04/024928. Further, plants can be made more tolerant to HPPD-inhibitor herbicides by adding into their genome a gene encoding an enzyme capable of metabolizing or degrading HPPD inhibitors, such as the CYP450 enzymes shown in WO 2007/103567 and WO 2008/150473.

Any of the above listed herbicide genes can be introduced into the claimed pennycress variety through a variety of means including but not limited to transformation and crossing.

3. Genes that confer or contribute to an altered grain characteristic, such as:

(A) Altered fatty acids, for example, by (1) down-regulation of stearoyl-ACP desaturase to increase stearic acid content of the plant. See, WO99/64579, (2) elevating oleic acid via FAD-2 gene modification and/or decreasing linolenic acid via FAD-3 gene modification, See, U.S. Pat. Nos. 6,063,947; 6,323,392; 6,372,965 and WO 93/11245, (3) altering conjugated linolenic or linoleic acid content, such as in WO 01/12800, (4) altering LEC1, AGP, Dek1, Superal1, milps, various Ipa genes such as Ipa1, Ipa3, hpt or hggt. For example, see WO 02/42424, WO 98/22604, WO 03/011015, U.S. Pat. Nos. 6,423,886, 6,197,561, 6,825,397, US Patent Application Publication Nos. 2003/0079247, 2003/0204870, WO02/057439, WO03/011015.

(B) Altered phosphorus content, for example, by the (1) introduction of a phytase-encoding gene would enhance breakdown of phytate, adding more free phosphate to the transformed plant, such as for example, using an *Aspergillus niger* phytase gene, (2) up-regulation of a gene that reduces phytate content.

(C) Altered carbohydrates effected, for example, by altering a gene for an enzyme that affects the branching pattern of starch, a gene altering thioredoxin. (See, U.S. Pat. No. 6,531,648). Exemplary genes include those encoding fructosyltransferase, levansucrase, alpha-amylase, invertase, branching enzyme II, UDP-D-xylose 4-epimerase, Fragile 1 and 2, Ref1, HCHL (4-hydroxycinnamoyl-CoA hydratase/lyase), C4H (cinnamate 4-hydroxylase), AGP (ADPglucose pyrophosphorylase). The fatty acid modification genes may also be used to affect starch content and/or composition through the interrelationship of the starch and oil pathways.

(D) Altered antioxidant content or composition, such as alteration of tocopherol or tocotrienols. For example, see, U.S. Pat. No. 6,787,683, US Patent Application Publication No. 2004/0034886 and WO 00/68393 involving the manipulation of antioxidant levels through alteration of a phytI prenyl transferase (ppt), WO 03/082899 through alteration of a homogentisate geranyl geranyl transferase (hggt).

(E) Altered essential seed amino acids. For example, see, U.S. Pat. No. 6,127,600 (method of increasing accumulation of essential amino acids in seeds), U.S. Pat. No. 6,080,913 (binary methods of increasing accumulation of essential amino acids in seeds), U.S. Pat. No. 5,990,389 (high lysine), WO99/40209 (alteration of amino acid compositions in seeds), WO99/29882 (methods for altering amino acid content of proteins), U.S. Pat. No. 5,850,016 (alteration of amino acid compositions in seeds), WO98/20133 (proteins with enhanced levels of essential amino acids), U.S. Pat. No. 5,885,802 (high methionine), U.S. Pat. No. 5,885,801 (high threonine), U.S. Pat. No. 6,664,445 (plant amino acid biosynthetic enzymes), U.S. Pat. No. 6,459,019 (increased lysine and threonine), U.S. Pat. No. 6,441,274 (plant tryptophan synthase beta subunit), U.S. Pat. No. 6,346,403 (methionine metabolic enzymes), U.S. Pat. No. 5,939,599 (high sulfur), U.S. Pat. No. 5,912,414 (increased methionine), WO98/56935 (plant amino acid biosynthetic enzymes), WO98/45458 (engineered seed protein having higher percentage of essential amino acids), WO98/42831 (increased lysine), U.S. Pat. No. 5,633,436 (increasing sulfur amino acid content), U.S. Pat. No. 5,559,223 (synthetic storage proteins with defined structure containing programmable levels of essential amino acids for improvement of the nutritional value of plants), WO96/01905 (increased threonine), WO95/15392 (increased lysine), US Patent Application Publication No. 2003/0163838, US Patent Application Publication No. 2003/0150014, US Patent Application Publication No. 2004/0068767, U.S. Pat. No. 6,803,498, WO01/79516, and WO00/09706 (Ces A: cellulose synthase), U.S. Pat. No. 6,194,638 (hemicellulose), U.S. Pat. No. 6,399,859 and US Patent Application Publication No. 2004/0025203 (UDPGdH), U.S. Pat. No. 6,194,638 (RGP).

(F) Reduced seed fiber content. For example, see, U.S. Pat. No. 10,709,151 (Low fiber pennycress meal and methods of making). Pennycress plants having reduced seed coat fiber, lighter-colored seed coat due to reduced proanthocyanidins content, increased protein content, and/or higher seed oil content can comprise one or more loss-of-function mutations in one or more genes that encode polypeptides involved in seed coat and embryo formation or can comprise transgenes that suppress expression of those genes. Polypeptides affecting these traits include, without limitation, TRANSPARENT TESTA1 (TT1) through TRANSPARENT TESTA19 (TT19) (e.g., TT1, TT2, TT3, TT4, TT5, TT6, TT7, TT8, TT9, TT10, TT12, TT13, TT15, TT16, TT18, and TT19), TRANSPARENT TESTA GLABRA1 and 2 (TTG1 and TTG2), GLABROUS 2 (GL2), GLABROUS 3 (GL3), ANR-BAN, and AUTO-INHIBITED H+-ATPASE 10 (AHA10).

(G) Reduced seed glucosinolate content. For example, see, U.S. Pat. No. 10,988,772 (Low glucosinolate pennycress meal and methods of making). Suppression of certain endogenous pennycress genes provide for reductions in sinigrin content. Pennycress plants having reduced sinigrin content can comprise one or more loss-of-function mutations in one or more genes that encode polypeptides involved in glucosinolate biosynthesis, in glucosinolate transport, in glucosinolate hydrolysis, regulating expression of genes encoding glucosinolate biosynthetic and/or transport genes (e.g., transcription factors) or can comprise transgenes or genome rearrangements that suppress expression of those biosynthetic, transporter, hydrolysis, or expression regulator (e.g., transcription factor) encoding genes. Polypeptides affecting these traits include, without limitation, AOP2, BCAT4, BCAT6, CYP79F1, CYP83A1, GTR1, GTR2, MYB28 (HAG1), MYB29, MYB76, TFP, BHLH05, IMD1, CYP79B3, MAM1, FMO-GS-Ox1, and UGT74B-1 polypeptides.

(H) Reduced seed erucic acid content. For example, see, U.S. Pat. No. 11,396,657 (Plants having increased oil quality). Loss-of-function modifications in the pennycress fatty acid elongase 1 (FAE1) gene provide for low levels of erucic acid (22:1).

4. Genes that control pollination, hybrid seed production or male-sterility:

There are several methods of conferring genetic male sterility available, such as multiple mutant genes at separate locations within the genome that confer male sterility, as disclosed in U.S. Pat. Nos. 4,654,465 and 4,727,219 to Brar et al., and chromosomal translocations as described by Patterson in U.S. Pat. Nos. 3,861,709 and 3,710,511. In addition to these methods, Albertsen et al., U.S. Pat. No. 5,432,068, describes a system of nuclear male sterility which includes: identifying a gene which is critical to male fertility; silencing this native gene which is critical to male fertility; removing the native promoter from the essential male fertility gene and replacing it with an inducible promoter; inserting this genetically engineered gene back into the plant; and thus creating a plant that is male sterile because the inducible promoter is not "on" resulting in the male fertility gene not being transcribed. Fertility is restored by inducing, or turning "on," the promoter, which in turn allows the gene that confers male fertility to be transcribed.

(A) Introduction of a deacetylase gene under the control of a tapetum-specific promoter and with the application of the chemical N-Ac-PPT. See, International Publication WO 01/29237.

(B) Introduction of various stamen-specific promoters. See, International Publications WO 92/13956 and WO 92/13957.

(C) Introduction of the barnase and the barstar genes. See, Paul et al., *Plant Mol. Biol.,* 19:611-622 (1992).

For additional examples of nuclear male and female sterility systems and genes, see also, U.S. Pat. Nos. 5,859, 341, 6,297,426, 5,478,369, 5,824,524, 5,850,014, and 6,265, 640, all of which are hereby incorporated by reference.

Also see, U.S. Pat. No. 5,426,041 (relating to a method for the preparation of a seed of a plant comprising crossing a male sterile plant and a second plant which is male fertile), U.S. Pat. No. 6,013,859 (molecular methods of hybrid seed production) and U.S. Pat. No. 6,037,523 (use of male tissue-preferred regulatory region in mediating fertility).

5. Genes that create a site for site specific DNA integration:

This includes the introduction of FRT sites that may be used in the FLP/FRT system and/or Lox sites that may be used in the Cre/loxP system. See, for example, Lyznik et al., Site-Specific Recombination for Genetic Engineering in Plants, *Plant Cell Rep,* 21:925-932 (2003) and WO 99/25821, which are hereby incorporated by reference. Other systems that may be used include the Gin recombinase of phage Mu (Maeser et al. (1991); Vicki Chandler, The Maize Handbook, Ch. 118 (Springer-Verlag 1994)); the Pin recombinase of *E. coli* (Enomoto et al. (1983)); and the R/RS system of the pSR1 plasmid (Araki et al. (1992)).

6. Genes that affect abiotic stress resistance:

Genes that affect abiotic stress resistance (including but not limited to flowering, pod and seed development, enhancement of nitrogen utilization efficiency, altered nitrogen responsiveness, drought resistance or tolerance, cold resistance or tolerance, and salt resistance or tolerance) and increased yield under stress. For example, see: WO 00/73475 where water use efficiency is altered through alteration of malate; U.S. Pat. Nos. 5,892,009, 5,965,705, 5,929,305, 5,891,859, 6,417,428, 6,664,446, 6,706,866, 6,717,034, 6,801,104, WO 2000/060089, WO 2001/026459, WO 2001/035725, WO 2001/034726, WO 2001/035727, WO 2001/036444, WO 2001/036597, WO 2001/036598, WO 2002/015675, WO 2002/017430, WO 2002/077185, WO 2002/079403, WO 2003/013227, WO 2003/013228, WO 2003/014327, WO 2004/031349, WO 2004/076638, WO 98/09521, and WO 99/38977 describing genes, including CBF genes and transcription factors effective in mitigating the negative effects of freezing, high salinity, and drought on plants, as well as conferring other positive effects on plant phenotype; U.S. Publ. No. 2004/0148654 and WO 01/36596, where abscisic acid is altered in plants resulting in improved plant phenotype, such as increased yield and/or increased tolerance to abiotic stress; WO 2000/006341, WO 04/090143, U.S. Pat. Nos. 7,531,723 and 6,992,237, where cytokinin expression is modified resulting in plants with increased stress tolerance, such as drought tolerance, and/or increased yield. See also, WO 02/02776, WO 2003/052063, JP 2002281975, U.S. Pat. No. 6,084,153, WO 01/64898, and U.S. Pat. Nos. 6,177,275 and 6,107,547 (enhancement of nitrogen utilization and altered nitrogen responsiveness). For ethylene alteration, see, U.S. Publ. Nos. 2004/0128719, 2003/0166197, and WO 2000/32761. For plant transcription factors or transcriptional regulators of abiotic stress, see, e.g., U.S. Publ. Nos. 2004/0098764 or 2004/0078852.

Other genes and transcription factors that affect plant growth and agronomic traits, such as yield, flowering, plant growth, and/or plant structure, can be introduced or introgressed into plants. See, e.g., WO 97/49811 (LHY), WO 98/56918 (ESD4), WO 97/10339, U.S. Pat. No. 6,573,430 (TFL), 6,713,663 (FT), 6,794,560, 6,307,126 (GAI), WO 96/14414 (CON), WO 96/38560, WO 01/21822 (VRN1), WO 00/44918 (VRN2), WO 99/49064 (GI), WO 00/46358 (FRI), WO 97/29123, WO 99/09174 (D8 and Rht), WO 2004/076638, and WO 004/031349 (transcription factors).

Methods for Pennycress Transformation

Numerous methods for plant transformation have been developed including biological and physical plant transformation protocols. See, for example, Miki et al., "Procedures for Introducing Foreign DNA into Plants," in *Methods in Plant Molecular Biology and Biotechnology,* Glick and Thompson Eds., CRC Press, Inc., Boca Raton, pp. 67-88 (1993). In addition, expression vectors and in-vitro culture methods for plant cell or tissue transformation and regeneration of plants are available. See, for example, Gruber et al., "Vectors for Plant Transformation," in *Methods in Plant Molecular Biology and Biotechnology,* Glick and Thompson Eds., CRC Press, Inc., Boca Raton, pp. 89-119 (1993).

A. *Agrobacterium*-mediated Transformation—One method for introducing an expression vector into plants is based on the natural transformation system of *Agrobacterium.* See, for example, Horsch et al., Science, 227:1229 (1985). *A. tumefaciens* and *A. rhizogenes* are plant pathogenic soil bacteria which genetically transform plant cells. The Ti and Ri plasmids of *A. tumefaciens* and *A. rhizogenes,* respectively, carry genes responsible for genetic transformation of the plant. See, for example, Kado, C. I., *Crit. Rev. Plant Sci.,* 10:1 (1991). Descriptions of *Agrobacterium* vector systems and methods for *Agrobacterium*-mediated gene transfer are provided by Gruber et al., supra, Miki et al., supra, and Moloney et al., *Plant Cell Reports,* 8:238 (1989). See also, U.S. Pat. No. 5,563,055 (Townsend and Thomas), issued Oct. 8, 1996.

B. Direct Gene Transfer—Several methods of plant transformation, collectively referred to as direct gene transfer, have been developed as an alternative to *Agrobacterium*-mediated transformation. A generally applicable method of plant transformation is microprojectile-mediated transformation where DNA is carried on the surface of microprojectiles measuring 1 to 4 µm. The expression vector is introduced into plant tissues with a biolistic device that accelerates the microprojectiles to speeds of 300 to 600 m/s which is sufficient to penetrate plant cell walls and membranes. Sanford et al., *Part. Sci. Technol.*, 5:27 (1987); Sanford, J. C., *Trends Biotech.*, 6:299 (1988); Klein et al., *Bio/Tech.*, 6:559-563 (1988); Sanford, J. C., *Physiol Plant*, 7:206 (1990); Klein et al., *Biotechnology*, 10:268 (1992). See also, U.S. Pat. No. 5,015,580 (Christou et al.), issued May 14, 1991 and U.S. Pat. No. 5,322,783 (Tomes et al.), issued Jun. 21, 1994.

Another method for physical delivery of DNA to plants is sonication of target cells. Zhang et al., *Bio/Technology*, 9:996 (1991). Alternatively, liposome and spheroplast fusion have been used to introduce expression vectors into plants. Deshayes et al., *EMBO J.*, 4:2731 (1985); Christou et al., *Proc Natl. Acad. Sci. USA*, 84:3962 (1987). Direct uptake of DNA into protoplasts using $CaCl_2$)) precipitation, polyvinyl alcohol or poly-L-ornithine have also been reported. Hain et al., *Mol. Gen. Genet.*, 199:161 (1985) and Draper et al., *Plant Cell Physiol.*, 23:451 (1982). Electroporation of protoplasts and whole cells and tissues have also been described (Donn et al., In Abstracts of VIIth International Congress on Plant Cell and Tissue Culture IAPTC, A2-38, p. 53 (1990); D'Halluin et al., *Plant Cell*, 4:1495-1505 (1992); and Spencer et al., *Plant Mol. Biol.*, 24:51-61 (1994)).

Following transformation of target tissues, expression of the above-described selectable marker genes allows for preferential selection of transformed cells, tissues, and/or plants, using regeneration and selection methods well known in the art.

The foregoing methods for transformation would typically be used for producing a transgenic variety. The transgenic variety could then be crossed with another (non-transformed or transformed) variety in order to produce a new transgenic variety. Alternatively, a genetic trait that has been engineered into a particular pennycress plant using the foregoing transformation techniques could be moved into another line using traditional backcrossing techniques that are well known in the plant breeding arts. For example, a backcrossing approach could be used to move an engineered trait from a public, non-elite variety into an elite variety, or from a variety containing a foreign gene in its genome into a variety or varieties that do not contain that gene. As used herein, "crossing" can refer to a simple x by y cross or the process of backcrossing depending on the context.

Genetic Marker Profiles

In addition to phenotypic observations, a plant can also be identified by its genotype. The genotype of a plant can be characterized through a genetic marker profile which can identify plants of the same variety, or a related variety, or be used to determine or validate a pedigree. Genetic marker profiles can be obtained by techniques such as Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs) (which are also referred to as Microsatellites), and Single Nucleotide Polymorphisms (SNPs). For example, see, Cregan et al., "An Integrated Genetic Linkage Map of the Soybean Genome," *Crop Science*, 39:1464-1490 (1999) and Berry et al., "Assessing Probability of Ancestry Using Simple Sequence Repeat Profiles: Applications to Maize Inbred Lines and Soybean Varieties," *Genetics*, 165:331-342 (2003), each of which are incorporated by reference herein in their entirety.

Particular markers used for these purposes are not limited to any particular set of markers, but are envisioned to include any type of marker and marker profile which provides a means of distinguishing varieties. One method of comparison is to use only homozygous loci for pennycress variety B3. In addition to being used for identification of pennycress variety B3, and plant parts and plant cells of pennycress variety B3, the genetic profile may be used to identify a pennycress plant produced through the use of pennycress variety B3 or to verify a pedigree for progeny plants produced through the use of pennycress variety B3. The genetic marker profile is also useful in breeding and developing backcross conversions.

The present disclosure provides in one embodiment a pennycress plant variety characterized by molecular and physiological data obtained from the representative sample of the variety deposited with the Provasoli-Guillard National Center for Marine Algae and Microbiota (NCMA). Further provided by the disclosure is a pennycress plant formed by the combination of the disclosed pennycress plant or plant cell with another pennycress plant or cell and comprising the homozygous alleles of the variety.

Means of performing genetic marker profiles using SSR polymorphisms are well known in the art. SSRs are genetic markers based on polymorphisms in repeated nucleotide sequences, such as microsatellites. A marker system based on SSRs can be highly informative in linkage analysis relative to other marker systems in that multiple alleles may be present. Another advantage of this type of marker is that, through use of flanking primers, detection of SSRs can be achieved, for example, by polymerase chain reaction (PCR), thereby eliminating the need for labor-intensive Southern hybridization. PCR detection is done by use of two oligonucleotide primers flanking the polymorphic segment of repetitive DNA. Repeated cycles of heat denaturation of the DNA followed by annealing of the primers to their complementary sequences at low temperatures, and extension of the annealed primers with DNA polymerase, comprise the major part of the methodology.

Following amplification, markers can be scored by electrophoresis of the amplification products. Scoring of marker genotype is based on the size of the amplified fragment, which may be measured by the number of base pairs of the fragment. While variation in the primer used or in laboratory procedures can affect the reported fragment size, relative values should remain constant regardless of the specific primer or laboratory used. When comparing varieties, it is preferable if all profiles are performed in the same lab.

In addition, plants and plant parts substantially benefiting from the use of pennycress variety B3 in their development, such as pennycress variety B3 comprising a backcross conversion, transgene, or gene edit, may be identified by having a molecular marker profile with a high percent identity to pennycress variety B3. Such a percent identity might be 95%, 96%, 97%, 98%, 99%, 99.5%, or 99.9% identical to pennycress variety B3.

A genetic marker profile of pennycress variety B3 can also be used to identify essentially derived varieties and other progeny varieties developed from the use of pennycress variety B3, as well as cells and other plant parts thereof. Progeny plants and plant parts produced using pennycress variety B3 may be identified by having a molecular marker profile of at least 25%, 30%, 35%, 40%, 45%, 50%, 55%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 99.5% genetic contribution from pennycress variety B3, as measured by either percent identity or percent similarity. Such progeny may be further characterized as being within a pedigree distance of pennycress variety B3, such as within 1, 2, 3, 4, or 5 or less cross-pollinations to a pennycress plant other than pennycress variety B3 or a plant that has pennycress variety B3 as a progenitor. Unique molecular profiles may be identified with other molecular tools such as SNPs and RFLPs.

Gene Conversions

When the term "pennycress plant" is used in the context of the present disclosure, this also includes a gene conversion of that variety. The term gene converted plant as used herein refers to those pennycress plants which are developed by a plant breeding technique called backcrossing wherein essentially all of the desired morphological and physiological characteristics of a variety are recovered in addition to the gene transferred into the line via the backcrossing technique. By "essentially all" as used herein in the context of morphological and physiological characteristics it is meant that the characteristics of a plant are recovered that are otherwise present when compared in the same environment, other than occasional variant traits that might arise during backcrossing or direct introduction of a transgene. It is understood that a locus introduced by backcrossing may or may not be transgenic in origin, and thus the term backcrossing specifically includes backcrossing to introduce loci that were created by genetic transformation.

Backcrossing methods can be used with the present disclosure to improve or introduce a characteristic into the variety. The term "backcrossing" as used herein refers to the repeated crossing of a hybrid progeny back to the recurrent parent, i.e., backcrossing 1, 2, 3, 4, 5, 6, 7, 8, or more times to the recurrent parent. The parental pennycress plant that contributes the gene for the desired characteristic is termed the nonrecurrent or donor parent. This terminology refers to the fact that the nonrecurrent parent is used one time in the backcross protocol and therefore does not recur. The parental pennycress plant to which the gene or genes from the nonrecurrent parent are transferred is known as the recurrent parent as it is used for several rounds in the backcrossing protocol (Poehlman & Sleper (1994); Fehr, Principles of Cultivar Development, pp. 261-286 (1987)). In a typical backcross protocol, the original variety of interest (recurrent parent) is crossed to a second variety (nonrecurrent parent) that carries the single gene of interest to be transferred. The resulting progeny from this cross are then crossed again to the recurrent parent and the process is repeated until a pennycress plant is obtained wherein essentially all of the morphological and physiological characteristics of the recurrent parent are recovered in the converted plant, in addition to the single transferred gene from the nonrecurrent parent.

The selection of a suitable recurrent parent is an important step for a successful backcrossing procedure. The goal of a backcross protocol is to alter or substitute traits or characteristics in the original line. To accomplish this, a gene or genes of the recurrent variety are modified or substituted with the desired gene or genes from the nonrecurrent parent, while retaining essentially all of the rest of the desired genetic, and therefore the desired physiological and morphological, constitution of the original line. The choice of the particular nonrecurrent parent will depend on the purpose of the backcross. One of the major purposes is to add some commercially desirable, agronomically important trait or traits to the plant. The exact backcrossing protocol will depend on the characteristics or traits being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many gene traits have been identified that are not regularly selected for in the development of a new line but that can be improved by backcrossing techniques. Gene traits may or may not be transgenic, examples of these traits include but are not limited to, herbicide resistance, resistance for bacterial, fungal, or viral disease, insect resistance, industrial usage, yield stability, yield enhancement, male sterility, reduced seed fiber content, modified seed color, earlier maturity, increased or modified seed protein composition, increased or modified seed oil or fatty acid content, reduced seed glucosinolate content, and shatter resistance. These genes are generally inherited through the nucleus. Several of these gene traits are described in U.S. Pat. Nos. 5,777,196; 5,948,957 and 5,969,212, the disclosures of which are specifically hereby incorporated by reference.

Tilling

TILLING (Targeting Induced Local Lesions IN Genomes) can be used to produce plants in which endogenous genes comprise a mutation. In a first step, introduced mutations such as novel single base pair changes are induced in a population of plants by treating seeds (or pollen) with a chemical mutagen, and then advancing plants to a generation where mutations will be stably inherited. DNA is extracted, and seeds are stored from all members of the population to create a resource that can be accessed repeatedly over time. For a TILLING assay, heteroduplex methods using specific endonucleases can be used to detect single nucleotide polymorphisms (SNPs). Alternatively, Next Generation Sequencing of DNA from pools of mutagenized plants can be used to identify mutants in the gene of choice. Typically, a mutation frequency of one mutant per 1000 plants in the mutagenized population is achieved. Using this approach, many thousands of plants can be screened to identify any individual with a single base change as well as small insertions or deletions (1-30 bp) in any gene or specific region of the genome. TILLING is further described in Slade and Knauf (2005), and Henikoff et al. (2004).

In addition to allowing efficient detection of mutations, high-throughput TILLING technology is ideal for the detection of natural polymorphisms. Therefore, interrogating an unknown homologous DNA by heteroduplexing to a known sequence reveals the number and position of polymorphic sites. Both nucleotide changes and small insertions and deletions are identified, including at least some repeat number polymorphisms. This has been called Ecotilling (Comai et al., 2004).

Genome Editing

Genome editing uses engineered nucleases such as RNA guided DNA endonucleases or nucleases composed of sequence specific DNA binding domains fused to a non-specific DNA cleavage module. These engineered nucleases enable efficient and precise genetic modifications by inducing targeted DNA double stranded breaks that stimulate the cell's endogenous cellular DNA repair mechanisms to repair the induced break. Such mechanisms include, for example, error prone non-homologous end joining (NHEJ) and homology directed repair (HDR).

In the presence of donor plasmid with extended homology arms, HDR can lead to the introduction of single or multiple transgenes to correct or replace existing genes. In the absence of donor plasmid, NHEJ-mediated repair yields small insertion or deletion mutations of the target that cause gene disruption. Engineered nucleases useful in the methods of the present disclosure include zinc finger nucleases (ZFNs), transcription activator-like (TAL) effector nucleases (TALEN) and CRISPR/Cas9 type nucleases.

Typically, nuclease encoded genes are delivered into cells by plasmid DNA, viral vectors or in vitro transcribed mRNA. A zinc finger nuclease (ZFN) comprises a DNA-binding domain and a DNA-cleavage domain, wherein the DNA binding domain is comprised of at least one zinc finger and is operatively linked to a DNA-cleavage domain. The zinc finger DNA-binding domain is at the N-terminus of the protein and the DNA-cleavage domain is located at the C-terminus of said protein.

A ZFN must have at least one zinc finger. In a preferred embodiment, a ZFN would have at least three zinc fingers in order to have sufficient specificity to be useful for targeted genetic recombination in a host cell or organism. Typically, a ZFN having more than three zinc fingers would have progressively greater specificity with each additional zinc finger.

The zinc finger domain can be derived from any class or type of zinc finger. In a particular embodiment, the zinc finger domain comprises the Cis2His2 type of zinc finger that is very generally represented, for example, by the zinc finger transcription factors TFIIIA or Sp1. In a preferred embodiment, the zinc finger domain comprises three Cis2His2 type zinc fingers. The DNA recognition and/or the binding specificity of a ZFN can be altered in order to accomplish targeted genetic recombination at any chosen site in cellular DNA. Such modification can be accomplished using known molecular biology and/or chemical synthesis techniques (see, for example, Bibikova et al., 2002).

The ZFN DNA-cleavage domain is derived from a class of non-specific DNA cleavage domains, for example the DNA-cleavage domain of a Type II restriction enzyme such as FoId (Kim et al., 1996). Other useful endonucleases may include, for example, HhaI, HindIII, Nod, BbvCI, EcoRI, BglI, and AlwI.

A transcription activator-like (TAL) effector nuclease (TALEN) comprises a TAL effector DNA binding domain and an endonuclease domain. TAL effectors are proteins of plant pathogenic bacteria that are injected by the pathogen into the plant cell, where they travel to the nucleus and function as transcription factors to turn on specific plant genes. The primary amino acid sequence of a TAL effector dictates the nucleotide sequence to which it binds. Thus, target sites can be predicted for TAL effectors, and TAL effectors can be engineered and generated for the purpose of binding to particular nucleotide sequences.

Fused to the TAL effector-encoding nucleic acid sequences are sequences encoding a nuclease or a portion of a nuclease, typically a nonspecific cleavage domain from a type II restriction endonuclease such as FokI (Kim et al., 1996). Other useful endonucleases may include, for example, HhaI, HindIII, Nod, BbvCI, EcoRI, BglI, and AhvI. The fact that some endonucleases (e.g., FokI) only function as dimers can be capitalized upon to enhance the target specificity of the TAL effector. For example, in some cases each FokI monomer can be fused to a TAL effector sequence that recognizes a different DNA target sequence, and only when the two recognition sites are in close proximity do the inactive monomers come together to create a functional enzyme. By requiring DNA binding to activate the nuclease, a highly site-specific restriction enzyme can be created.

A sequence-specific TALEN can recognize a particular sequence within a preselected target nucleotide sequence present in a cell. Thus, in some embodiments, a target nucleotide sequence can be scanned for nuclease recognition sites, and a particular nuclease can be selected based on the target sequence. In other cases, a TALEN can be engineered to target a particular cellular sequence.

Distinct from the site-specific nucleases described above, the clustered regulatory interspaced short palindromic repeats (CRISPR)/Cas system provides an alternative to ZFNs and TALENs for inducing targeted genetic alterations, via RNA-guided DNA cleavage.

CRISPR systems rely on CRISPR RNA (crRNA) and transactivating chimeric RNA (tracrRNA) for sequence-specific cleavage of DNA. Three types of CRISPR/Cas systems exist: in type II systems, Cas9 serves as an RNA-guided DNA endonuclease that cleaves DNA upon crRNA-tracrRNA target recognition. CRISPR RNA base pairs with tracrRNA to form a two-RNA structure that guides the Cas9 endonuclease to complementary DNA sites for cleavage.

The CRISPR system can be portable to plant cells by co-delivery of plasmids expressing the Cas endonuclease and the necessary crRNA components. The Cas endonuclease may be converted into a nickase to provide additional control over the mechanism of DNA repair (Cong et al., 2013).

CRISPRs are typically short partially palindromic sequences of 24-40 bp containing inner and terminal inverted repeats of up to 11 bp. Although isolated elements have been detected, they are generally arranged in clusters (up to about 20 or more per genome) of repeated units spaced by unique intervening 20-58 bp sequences. CRISPRs are generally homogenous within a given genome with most of them being identical. However, there are examples of heterogeneity in, for example, the Archaea (Mojica et al., 2000).

Tissue Culture

Further reproduction of the variety can occur by tissue culture and regeneration. Tissue culture of various tissues and regeneration of plants therefrom is well known and widely published. For example, reference may be had to Komatsuda, T. et al., Crop Sci., 31:333-337 (1991); Stephens, P. A. et al., Theor. Appl. Genet., 82:633-635 (1991); Komatsuda, T. et al., Plant Cell, Tissue and Organ Culture, 28:103-113 (1992); Dhir, S. et al., Plant Cell Reports, 11:285-289 (1992); Pandey, P. et al., Japan J. Breed., 42:1-5 (1992); and Shetty, K. et al., Plant Science, 81:245-251 (1992); as well as U.S. Pat. No. 5,024,944, issued Jun. 18, 1991 to Collins et al. and U.S. Pat. No. 5,008,200, issued Apr. 16, 1991 to Ranch et al. Thus, another embodiment of this disclosure is to provide cells which upon growth and differentiation produce pennycress plants having the morphological and physiological characteristics of pennycress variety B3.

As used herein, the term "tissue culture" indicates a composition comprising isolated cells of the same or a different type or a collection of such cells organized into parts of a plant. Exemplary types of tissue cultures are protoplasts, calli, plant clumps, and plant cells that can generate tissue culture that are intact in plants or parts of plants, such as embryos, pollen, flowers, seeds, petioles, leaves, stems, roots, root tips, anthers, pistils, and the like. Means for preparing and maintaining plant tissue culture are well known in the art. By way of example, a tissue culture comprising organs has been used to produce regenerated plants. U.S. Pat. Nos. 5,959,185, 5,973,234, and 5,977,445 describe certain techniques, the disclosures of which are incorporated herein by reference.

Additional Breeding Methods

This disclosure is directed to methods for producing a pennycress plant by crossing a first parent pennycress plant with a second parent pennycress plant wherein either the first or second parent pennycress plant is variety B3. The other parent may be any other pennycress plant. Any such methods using pennycress variety B3 are part of this disclosure: selfing, sibbing, backcrosses, mass selection, pedigree breeding, bulk selection, hybrid production, crosses to populations, and the like. These methods are well known in the art and some of the more commonly used breeding methods are described below. Descriptions of breeding methods can be found in one of several reference books (e.g., Allard, Principles of Plant Breeding (1960); Simmonds, Principles of Crop Improvement (1979); Sneep et al. (1979); Fehr, "Breeding Methods for Cultivar Development," Chapter 7, Soybean Improvement, Production and Uses, 2nd ed., Wilcox editor (1987)).

The following describes breeding methods that may be used with pennycress variety B3 in the development of further pennycress plants. One such embodiment is a method for developing a variety B3 progeny pennycress plant in a pennycress plant breeding program comprising: obtaining the pennycress plant, or a part thereof, of variety B3, utilizing the plant, or plant part, as a source of breeding material, and selecting a pennycress variety B3 progeny plant with molecular markers in common with variety B3 and/or with morphological and/or physiological characteristics selected from the characteristics listed in Table 1. Breeding steps that may be used in the pennycress plant breeding program include pedigree breeding, backcrossing, mutation breeding, and recurrent selection. In conjunction with these steps, techniques such as RFLP-enhanced selection, genetic marker enhanced selection (for example, SSR markers), and the making of double haploids may be utilized.

Another method involves producing a population of pennycress variety B3 progeny pennycress plants, comprising crossing variety B3 with another pennycress plant, thereby producing a population of pennycress plants which, on average, derive 50% of their alleles from pennycress variety B3. A plant of this population may be selected and repeatedly selfed or sibbed with a pennycress variety resulting from these successive filial generations. One embodiment of this disclosure is the pennycress variety produced by this method and that has obtained at least 50% of its alleles from pennycress variety B3.

One of ordinary skill in the art of plant breeding would know how to evaluate the traits of two plant varieties to determine if there is no significant difference between the two traits expressed by those varieties. For example, see, Fehr and Walt, Principles of Cultivar Development, pp. 261-286 (1987). Thus, the disclosure includes pennycress variety B3 progeny plants comprising a combination of at least two variety B3 traits selected from those listed in Table 1, so that the progeny plant is not significantly different for the traits than pennycress variety B3 as determined at the 5% significance level when grown in the same environmental conditions. Using techniques described herein, molecular markers may be used to identify the progeny plant as a pennycress variety B3 progeny plant. Mean trait values may be used to determine whether trait differences are significant, and preferably the traits are measured on plants grown under the same environmental conditions. Once such a variety is developed, its value is substantial since it is important to advance the germplasm base as a whole in order to maintain or improve traits such as yield, disease resistance, pest resistance, and plant performance in extreme environmental conditions.

Progeny of pennycress variety B3 may also be characterized through their filial relationship with pennycress variety B3, as for example, being within a certain number of breeding crosses of pennycress variety B3. A breeding cross is a cross made to introduce new genetics into the progeny, and is distinguished from a cross, such as a self or a sib cross, made to select among existing genetic alleles. The lower the number of breeding crosses in the pedigree, the closer the relationship between pennycress variety B3 and its progeny. For example, progeny produced by the methods described herein may be within 1, 2, 3, 4, or 5 breeding crosses of pennycress variety B3.

Seed Treatments and Cleaning

Methods of harvesting the seed of the pennycress variety B3 as seed for planting are provided. Embodiments include cleaning the seed, treating the seed, and/or conditioning the seed. Cleaning the seed is understood in the art to include removal of foreign debris such as one or more of weed seed, chaff, and plant matter, from the seed. Conditioning the seed is understood in the art to include controlling the temperature and rate of dry down of the seed and storing seed in a controlled temperature environment. Seed treatment is the application of a composition to the surface of the seed such as a coating or powder. Methods for producing a treated seed include the step of applying a composition to the seed or seed surface. Seeds are provided which have on the surface a composition. Biological active components such as bacteria can also be used as a seed treatment. Some examples of compositions are insecticides, fungicides, pesticides, antimicrobials, germination inhibitors, germination promoters, cytokinins, and nutrients.

Seed material can be treated, typically surface treated, with a composition comprising combinations of chemical or biological herbicides, herbicide safeners, insecticides, fungicides, germination inhibitors and enhancers, nutrients, plant growth regulators and activators, bactericides, nematicides, avicides and/or molluscicides. These compounds are typically formulated together with further carriers, surfactants or application-promoting adjuvants customarily employed in the art of formulation. The coatings may be applied by impregnating propagation material with a liquid formulation or by coating with a combined wet or dry formulation.

Some seed treatments that may be used on crop seed include, but are not limited to, one or more of abscisic acid, acibenzolar-S-methyl, avermectin, amitrol, azaconazole, azospirillum, azadirachtin, azoxystrobin, *Bacillus* spp. (including one or more of *cereus, firmus, megaterium, pumilis, sphaericus, subtilis* and/or *thuringiensis*), *Bradyrhizobium* spp. (including one or more of *betae, canariense, elkanii, iriomotense, japonicum,* liaonigense, *pachyrhizi* and/or *yuanmingense*), captan, carboxin, chitosan, clothianidin, copper, cyazypyr, difenoconazole, etidiazole, fipronil, fludioxonil, fluoxastrobin, fluquinconazole, flurazole, fluxofenim, gibberellic acid, harpin protein, imazalil, imidacloprid, ipconazole, isoflavenoids, lipo-chitooligosaccharide, mancozeb, manganese, maneb, mefenoxam, metalaxyl, metconazole, myclobutanil, PCNB (EPA registration number 00293500419, containing quintozen and terrazole), penflufen, *penicillium*, penthiopyrad, permethrine, picoxystrobin, prothioconazole, pyraclostrobin, rynaxypyr, S-metolachlor, saponin, sedaxane, TCMTB (2-(thiocyanom-ethylthio) benzothiazole), tebuconazole, thiabendazole, thia-methoxam, thiocarb, thiram, tolclofos-methyl, triadimenol, *trichoderma*, trifloxystrobin, triticonazole and/or zinc.

While a number of exemplary aspects and embodiments have been discussed above, those of skill in the art will that certain changes and modifications such as single gene modifications and mutations, somoclonal variants, variant individuals selected from large populations of the plants of the instant variety and the like may be practiced within the scope of the disclosure, as limited only by the scope of the appended claims All references, including publications, patents, and patent applications, cited herein are hereby incorporated by reference to the same extent as if each reference were individually and specifically indicated to be incorporated by reference and were set forth in its entirety herein.

Embodiments of the Disclosure

The following represent a nonlimiting list of embodiments of the disclosure herein.

1. A seed of pennycress variety B3, wherein a sample of seed of the variety has been deposited under NCMA Accession No. 202208005.

2. A pennycress plant produced by growing the seed of embodiment 1.

3. A pennycress plant, or a part thereof, having all the physiological and morphological characteristics of the pennycress plant of embodiment 2.

4. A pennycress plant, or a part thereof, which does not significantly differ from the plant of embodiment 2 when determined at the 5% significance level when grown under the same environmental conditions.

5. A part of the pennycress plant of embodiment 2, wherein the part is a microspore, pollen, an ovary, an ovule, an embryo sac, an egg cell, pericarp, a root, a leaf, an inflorescence, a stem, a flower, a pod, a cell, or a protoplast.

6. A tissue culture of regenerable cells or protoplasts from the pennycress plant of embodiment 2.

7. The tissue culture of embodiment 6, wherein the cells of the tissue culture are produced from a plant part, wherein the plant part is an embryo, a meristematic cell, a leaf, a cotyledon, a hypocotyl, a stem, a root, a root tip, a pistil, an anther, a flower, a pod, a seed, or pollen.

8. A pennycress plant regenerated from the tissue culture of embodiment 6, wherein the plant has all of the morphological and physiological characteristics of variety B3, wherein a sample of seed of the variety has been deposited under NCMA Accession No. 202208005.

9. A method of vegetatively propagating a plant of pennycress variety B3, the method comprising:
collecting tissue capable of being propagated from a plant of pennycress variety B3, wherein a sample of seed of the variety was deposited under NCMA Accession No. 202208005;
cultivating the tissue to obtain proliferated shoots;
rooting the proliferated shoots to obtain a rooted plantlet; and
optionally growing a pennycress plant from the rooted plantlet.

10. A pennycress plant or rooted plantlet produced by the method of embodiment 9.

11. A method for producing a progeny plant of pennycress variety B3, comprising:
crossing the pennycress plant of embodiment 2 with itself or with another pennycress plant;
harvesting the resultant seed; and
growing the seed.

12. A method for producing a hybrid pennycress seed, wherein the method comprises:
crossing the pennycress plant of embodiment 2 with a plant of a different pennycress variety; and
harvesting the resultant hybrid pennycress seed.

13. A hybrid pennycress seed produced by the method of embodiment 12.

14. A hybrid pennycress plant, or a part thereof, produced by growing the hybrid pennycress seed of embodiment 13.

15. A method of producing a pennycress plant derived from pennycress variety B3, the method comprising the steps of:
(a) crossing the plant of embodiment 2 with a second pennycress plant to produce a progeny plant;
(b) crossing the progeny plant of step (a) with itself or the second pennycress plant in step (a) to produce a seed
(c) growing a progeny plant of a subsequent generation from the seed produced in step (b);
(d) crossing the progeny plant of a subsequent generation of step (c) with itself or the second pennycress plant in step (a) to produce a pennycress plant derived from pennycress variety B3.

16. A plant of pennycress variety B3, a sample of seed of the variety having been deposited under NCMA Accession No. 202208005, wherein the plant further comprises a mutation of an endogenous gene.

17. The plant of embodiment 16, wherein the mutation of the endogenous gene is a loss-of-function mutation.

18. The plant of embodiment 16, wherein the mutation of the endogenous gene confers a desired trait, and wherein the desired trait comprises herbicide resistance, insect resistance, resistance to bacterial disease, fungal disease, or viral disease, male sterility, reduced seed fiber content, modified seed color, earlier maturity, increased or modified seed protein composition, increased or modified seed oil or fatty acid content, reduced seed glucosinolate content, or shatter resistance.

19. The plant of embodiment 18, wherein the desired trait comprises reduced seed fiber content, modified seed color, earlier maturity, increased or modified seed protein composition, increased or modified seed oil or fatty acid content, and reduced erucic acid content.

20. The plant of embodiment 16, wherein the endogenous gene is TRANSPARENT TESTA1 (TT1), TT2, TT3, TT4, TT5, TT6, TT7, TT8, TT9, TT10, TT12, TT13, TT15, TT16, TT18, TT19, TRANSPARENT TESTA GLABRA1 (TTG1), TTG2, GLABROUS 2 (GL2), (GL3), ANR-BAN, or AUTOINHIBITED H+-AT-PASE 10 (AHA10).

21. The plant of embodiment 16, wherein the endogenous gene is FATTY ACID ELONGASE 1 (FAE1).

22. The plant of embodiment 16, wherein the plant comprises a desired trait and otherwise comprises all of the morphological and physiological characteristics of a pennycress plant of variety B3 when grown under the same environmental conditions.

23. A method of producing a modified pennycress plant, the method comprising mutating an endogenous gene in a pennycress plant or plant part of pennycress variety B3, wherein a sample of seed of the variety has been deposited under NCMA Accession No. 202208005.

24. The method of embodiment 23, wherein the mutation of the endogenous gene confers a desired trait, and wherein the desired trait comprises herbicide resistance, insect resistance, resistance to bacterial disease, fungal disease, or viral disease, male sterility, reduced seed fiber content, modified seed color, earlier maturity, increased or modified seed protein composition, increased or modified seed oil or fatty acid content, reduced seed glucosinolate content, or shatter resistance.

25. The method of embodiment 23, wherein the desired trait comprises reduced seed fiber content, modified seed color, earlier maturity, increased or modified seed protein composition, increased or modified seed oil or fatty acid content, and reduced erucic acid content.

26. The method of embodiment 23, wherein the endogenous gene is mutated by targeted gene editing.

27. A modified pennycress plant produced by the method of embodiment 23.

28. The modified pennycress plant of embodiment 27, wherein the modified pennycress plant comprises a desired trait and otherwise has all of the physiological and morphological characteristics of pennycress variety B3.

29. A method for producing a hybrid pennycress seed, wherein the method comprises:

crossing the pennycress plant of embodiment 16 with a plant of a different pennycress variety; and harvesting the resultant hybrid pennycress seed.

30. A hybrid pennycress seed produced by the method of embodiment 29.

31. A hybrid pennycress plant, or a part thereof, produced by growing the hybrid pennycress seed of embodiment 30.

32. A method of introducing a desired trait into pennycress variety B3, the method comprising:

(a) crossing a plant of pennycress variety B3, wherein a representative sample of seed has been deposited under NCMA Accession No. 202208005, with a plant of another pennycress variety that comprises the desired trait to produce an $F_1$ progeny plant;

(b) selecting at least a first progeny plant that comprises the desired trait to produce a selected progeny plant;

(c) crossing the selected progeny plant with a plant of pennycress variety B3 to produce at least a first backcross progeny plant that comprises the desired trait;

(d) selecting for at least one backcross progeny plant that has the desired trait and otherwise all of the physiological and morphological characteristics of a plant of pennycress variety B3 to produce at least one selected backcross progeny plant; and (e) repeating steps (c) and (d) three or more times in succession to produce a selected fourth or higher backcross progeny plant that comprises the desired trait and otherwise all of the physiological and morphological characteristics of a plant of pennycress variety B3.

33. The method of embodiment 32, wherein the desired trait comprises herbicide resistance, insect resistance, resistance to bacterial disease, fungal disease, or viral disease, male sterility, reduced seed fiber content, modified seed color, earlier maturity, increased or modified seed protein composition, increased or modified seed oil or fatty acid content, reduced seed glucosinolate content, or shatter resistance.

34. The method of embodiment 32, wherein the desired trait comprises reduced seed fiber content, modified seed color, earlier maturity, increased or modified seed protein composition, increased or modified seed oil or fatty acid content, and reduced erucic acid content.

35. A pennycress plant produced by the method of embodiment 32.

36. The pennycress plant of embodiment 35, wherein the plant comprises a desired trait and otherwise comprises all of the physiological and morphological characteristics of a plant of pennycress variety B3.

37. The pennycress plant of embodiment 35, wherein the plant does not significantly differ from a plant of pennycress variety B3 when determined at the 5% significance level when grown under the same environmental conditions 38. A method of producing a plant of pennycress variety B3 comprising at least one new trait, the method comprising:

introducing a transgene conferring the at least one new trait into a plant of pennycress variety B3, wherein a sample of seed of the variety has been deposited under NCMA Accession No. 202208005.

39. The method of embodiment 38, wherein the new trait comprises herbicide resistance, insect resistance, resistance to bacterial disease, fungal disease, or viral disease, male sterility, reduced seed fiber content, modified seed color, earlier maturity, increased or modified seed protein composition, increased or modified seed oil or fatty acid content, reduced seed glucosinolate content, or shatter resistance.

40. A pennycress plant produced by the method of embodiment 38, wherein the plant comprises the new trait and otherwise comprises all of the physiological and morphological characteristics of a plant of pennycress variety B3.

41. A method of introducing a mutation into the genome of pennycress variety B3, the method comprising applying a mutagen to the pennycress plant of embodiment 2, or a part thereof, wherein the mutagen is selected from ethyl methanesulfonate, gamma-rays, and sodium azide, and wherein the resulting plant comprises a genome mutation.

42. A mutagenized pennycress plant produced by the method of embodiment 41, wherein the mutagenized pennycress plant comprises the genome mutation and otherwise comprises all of the morphological and physiological characteristics of pennycress variety B3

43. A plant of pennycress variety B3, a sample of seed of the variety having been deposited under NCMA Accession No. 202208005, wherein the plant further comprises at least one locus conversion.

44. The plant of embodiment 43, wherein the locus conversion confers the plant with a trait selected from herbicide resistance, insect resistance, disease resistance, male sterility, reduced seed fiber content, modified seed color, earlier maturity, increased or modified seed protein composition, increased or modified seed oil or fatty acid content, reduced seed glucosinolate content, and shatter resistance.

45. The plant of embodiment 43, wherein the plant comprises the locus conversion and otherwise comprises all of the morphological and physiological characteristics of pennycress variety B3.

46. A chromosome of a plant of pennycress variety B3, a sample of seed of the variety having been deposited under NCMA Accession No. 202208005.

47. A plant comprising one or more copies of the chromosome of embodiment 46.

48. A method of producing a modified pennycress plant, wherein the method comprises mutation, transformation, gene conversion, genome editing, RNA interference, or gene silencing of the plant of embodiment 2.

49. A method of producing a commodity plant product, the method comprising obtaining the plant of embodiment 16 or a part thereof and producing the commodity plant product therefrom.

50. The method of embodiment 49, wherein the commodity plant product comprises carbohydrate, silage, oil, or protein.

51. A method of comparing and/or characterizing the genotype of a plant of pennycress variety B3, a sample of seed of which has been deposited under NCMA Accession No. 202208005, comprising:

obtaining a sample of nucleic acids from the plant of pennycress variety B3;

obtaining a sample of nucleic acids from a plant of a reference pennycress variety;

comparing the nucleic acids obtained from the plant of pennycress variety B3 to the sample of nucleic acids obtained from the reference plant, and detecting a plurality of polymorphisms between the two nucleic acid samples, wherein the plurality of polymorphisms is indicative of pennycress variety B3 and/or gives rise to the expression of any one or more, or all, of the physiological and morphological characteristics of pennycress variety B3.

52. A method for developing a pennycress variety in a pennycress plant breeding program, comprising applying plant breeding techniques comprising recurrent selection, backcrossing, pedigree breeding, marker enhanced selection, mutation breeding, or genetic modification to the pennycress plant of embodiment 2, or its parts, to develop a pennycress variety.

DEPOSIT

Applicant has made a deposit of at least 625 seeds of pennycress variety B3 under the Budapest Treaty with the Provasoli-Guillard National Center for Marine Algae and Microbiota (NCMA), 60 Bigelow Drive, East Boothbay, Me. 04544, USA, with NCMA Accession No. 202208005. The seeds deposited with the NCMA on Aug. 25, 2022 were taken from the deposit maintained by CoverCress Inc., 1249 N. Warson Rd, St. Louis, MO 63132 since prior to the filing date of this application. Access to this deposit will be available during the pendency of the application to the Commissioner of Patents and Trademarks and persons determined by the Commissioner to be entitled thereto upon request. Upon issue of claims, the Applicant(s) will make available to the public, pursuant to 37 CFR 1.808, a deposit of at least 625 seeds of pennycress variety B3 with the NCMA. This deposit will be maintained in the depository, which is a public depository, for a period of 30 years, or 5 years after the most recent request, or for the enforceable life of the patent, whichever is longer, and will be replaced if it becomes nonviable during that period. All restrictions imposed by the depositor on the availability to the public of the deposited material will be irrevocably removed upon the granting of the patent. Additionally, Applicant has complied or will comply with all the requirements of 37 C.F.R. §§ 1.801-1.809, including providing an indication of the viability of the sample. Applicant has no authority to waive any restrictions imposed by law on the transfer of biological material or its transportation in commerce. Applicant does not waive any infringement of their rights granted under this patent or under the Plant Variety Protection Act (7 USC 2321 et seq.).

What is claimed is:

1. A seed of pennycress variety B3, wherein a representative sample of seed of the variety has been deposited under NCMA Accession No. 202208005.

2. A pennycress plant produced by growing the seed of claim 1.

3. A part of the pennycress plant of claim 2, wherein the part is a microspore, pollen, an ovary, an ovule, an embryo sac, an egg cell, pericarp, a root, a leaf, an inflorescence, a stem, a flower, a pod, a cell, or a protoplast.

4. A tissue culture of regenerable cells or protoplasts from the pennycress plant of claim 2, produced from an embryo, a meristematic cell, a leaf, a cotyledon, a hypocotyl, a stem, a root, a root tip, a pistil, an anther, a flower, a pod, a seed, or pollen of the pennycress plant of claim 2.

5. A pennycress plant regenerated from the tissue culture of claim 4, wherein the plant has all of the morphological and physiological characteristics of variety B3, wherein a representative sample of seed of the variety has been deposited under NCMA Accession No. 202208005.

6. A method of vegetatively propagating a plant of pennycress variety B3, the method comprising:

collecting tissue capable of being propagated from a plant of pennycress variety B3, wherein a representative sample of seed of the variety was deposited under NCMA Accession No. 202208005;

cultivating the tissue to obtain proliferated shoots;

rooting the proliferated shoots to obtain a rooted plantlet; and optionally growing a pennycress plant from the rooted plantlet.

7. A pennycress plant or rooted plantlet produced by the method of claim 6, wherein the plant has all of the morphological and physiological characteristics of pennycress variety B3.

8. A method for producing a hybrid pennycress seed, wherein the method comprises:

crossing the pennycress plant of claim 2 with a plant of a different pennycress variety; and harvesting the resultant hybrid pennycress seed.

9. An $F_1$ hybrid pennycress seed produced by the method of claim 8.

10. An $F_1$ hybrid pennycress plant, or a part thereof, produced by growing the $F_1$ hybrid pennycress seed of claim 9.

11. A method of producing a pennycress plant derived from pennycress variety B3, the method comprising the steps of:

(a) crossing the plant of claim 2 with a second pennycress plant to produce a progeny plant;

(b) crossing the progeny plant of step (a) with itself or the second pennycress plant in step (a) to produce a seed;

(c) growing a progeny plant of a subsequent generation from the seed produced in step (b);

(d) crossing the progeny plant of a subsequent generation of step (c) with itself or the second pennycress plant in step (a) to produce a pennycress plant derived from pennycress variety B3.

12. A method of producing a plant of pennycress variety B3 comprising at least one desired trait, the method comprising introducing a single locus conversion conferring the desired trait into pennycress variety B3, wherein a representative sample of seed of the variety has been deposited under NCMA Accession No. 202208005.

13. A pennycress plant produced by the method of claim 12, wherein the plant comprises one single locus conversion and otherwise all of the morphological and physiological characteristics of pennycress variety B3.

14. The plant of claim 13, wherein the single locus conversion confers said plant with a desired trait, and wherein the desired trait comprises herbicide resistance, insect resistance, resistance to bacterial disease, fungal disease, or viral disease, male sterility, reduced seed fiber content, modified seed color, earlier maturity, increased or modified seed protein composition, increased or modified seed oil or fatty acid content, reduced seed glucosinolate content, reduced erucic acid content, and/or shatter resistance.

15. A method of producing a modified pennycress plant, the method comprising mutating one or more endogenous genes in the pennycress plant of claim 2 or a plant part thereof.

16. The method of claim 15, wherein the mutation of the one or more endogenous genes confers a desired trait, and wherein the desired trait comprises herbicide resistance, insect resistance, resistance to bacterial disease, fungal disease, or viral disease, male sterility, reduced seed fiber content, modified seed color, earlier maturity, increased or modified seed protein composition, increased or modified seed oil or fatty acid content, reduced seed glucosinolate content, reduced erucic acid content, and/or shatter resistance.

17. A modified pennycress plant produced by the method of claim 16, wherein the plant comprises the desired trait and otherwise all of the morphological and physiological characteristics of pennycress variety B3.

18. A method for producing a hybrid pennycress seed, wherein the method comprises:

crossing the pennycress plant of claim 13 with a plant of a different pennycress variety; and harvesting the resultant hybrid pennycress seed.

19. An $F_1$ hybrid pennycress seed produced by the method of claim 18.

20. An $F_1$ hybrid pennycress plant, or a part thereof, produced by growing the $F_1$ hybrid pennycress seed of claim 19.

21. A method of introducing a desired trait into pennycress variety B3, the method comprising:

(a) crossing a plant of pennycress variety B3, wherein a representative sample of seed has been deposited under NCMA Accession No. 202208005, with a plant of another pennycress variety that comprises the desired trait to produce an $F_1$ progeny plant;

(b) selecting at least a first $F_1$ progeny plant that comprises the desired trait to produce a selected $F_1$ progeny plant;

(c) crossing the selected $F_1$ progeny plant with a plant of pennycress variety B3 to produce at least a first backcross progeny plant that comprises the desired trait;

(d) selecting for at least one backcross progeny plant that has the desired trait and otherwise all of the physiological and morphological characteristics of a plant of pennycress variety B3 to produce at least one selected backcross progeny plant; and (e) repeating steps (c) and (d) three or more times in succession to produce a selected fourth or higher backcross progeny plant that comprises the desired trait and otherwise all of the physiological and morphological characteristics of a plant of pennycress variety B3.

22. A pennycress plant produced by the method of claim 21.

23. A method of introducing a mutation into the genome of pennycress variety B3, the method comprising applying a mutagen to the pennycress plant of claim 2, or a part thereof, wherein the mutagen is selected from ethyl methanesulfonate, gamma-rays, and sodium azide, and wherein the resulting plant comprises a genome mutation.

24. A plant comprising at least a first set of chromosomes of a plant of pennycress variety B3, a representative sample of seed of the variety having been deposited under NCMA Accession No. 202208005.

25. A method of producing a modified pennycress plant, wherein the method comprises mutation, transformation, gene conversion, genome editing, RNA interference, or gene silencing of the plant of claim 2.

26. A method of producing a commodity plant product, the method comprising producing the commodity plant product from the plant of claim 12 or a part thereof, wherein the commodity plant product comprises carbohydrate, silage, oil, or protein.

27. A method of comparing and/or characterizing the genotype of a plant of pennycress variety B3, a representative sample of seed of which has been deposited under NCMA Accession No. 202208005, comprising:

obtaining a sample of nucleic acids from the plant of pennycress variety B3;

obtaining a sample of nucleic acids from a plant of a distinct pennycress variety; and comparing the nucleic acids obtained from the plant of pennycress variety B3 to the sample of nucleic acids obtained from the plant of the distinct pennycress variety.

28. A method for developing a pennycress variety in a pennycress plant breeding program, comprising applying plant breeding techniques comprising recurrent selection, backcrossing, pedigree breeding, marker enhanced selection, mutation breeding, or genetic modification to the pennycress plant of claim 2, or its parts, to develop a pennycress variety.

* * * * *